(12) United States Patent
Reddy

(10) Patent No.: US 10,172,870 B2
(45) Date of Patent: Jan. 8, 2019

(54) METHOD OF TREATING ORGANOPHOSPHATE INTOXICATION BY ADMINISTRATION OF NEUROSTEROIDS

(71) Applicant: THE TEXAS A&M UNIVERSITY SYSTEM, College Station, TX (US)

(72) Inventor: Doodipala Samba Reddy, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/508,233

(22) PCT Filed: Sep. 1, 2015

(86) PCT No.: PCT/US2015/047914
§ 371 (c)(1),
(2) Date: Mar. 2, 2017

(87) PCT Pub. No.: WO2016/036724
PCT Pub. Date: Mar. 10, 2016

(65) Prior Publication Data
US 2017/0246188 A1    Aug. 31, 2017

Related U.S. Application Data

(60) Provisional application No. 62/044,635, filed on Sep. 2, 2014.

(51) Int. Cl.
*A61K 31/57* (2006.01)
*A61K 31/565* (2006.01)
*A61K 31/573* (2006.01)

(52) U.S. Cl.
CPC ............ *A61K 31/57* (2013.01); *A61K 31/565* (2013.01); *A61K 31/573* (2013.01)

(58) Field of Classification Search
CPC ..... A61K 31/57; A61K 31/565; A61K 31/573
See application file for complete search history.

(56) References Cited

U.S. PATENT DOCUMENTS

| 5,521,215 A | 5/1996 | Kloog Y et al. ............... 514/454 |
| 5,705,188 A | 1/1998 | Junichi et al. ................ 424/450 |

(Continued)

FOREIGN PATENT DOCUMENTS

| WO | WO/1993/003732 | 3/1993 |
| WO | WO/1993/018053 | 9/1993 |

(Continued)

OTHER PUBLICATIONS

Apland, J. P. et al. (2014) "The Limitations of Diazepam as a Treatment for Nerve Agent-Induced Seizures and Neuropathology in Rats: Comparison with UBP302," *Journal of Pharmacology and Experimental Therapeutics* 351(2), 359.

(Continued)

*Primary Examiner* — Savitha M Rao
(74) *Attorney, Agent, or Firm* — Medlen & Carroll, LLP

(57) ABSTRACT

The present invention provides new compositions and methods for treating and/or reversing organophosphate intoxication, manifested by both cholinergic and non-cholinergic crisis, in a mammal resulting from exposure to organophosphate compounds. The neurosteroidal compounds of this invention are those having the general structural formula of pregnane, androstane, 19-norandrostanes, and norpregnane with further moieties as defined herein. These compounds include, but are not limited to, ganaxolone, pregnanolone, and androstanediol and their analogs, salts and prodrugs. The present invention further relates to combining a therapeutically effective amount of a neurosteroidal compound with a standard organophosphate antidote (e.g. atropine, pralidoxime). The data suggests that neurosteroids are effective or more effective than benzodiazepines, whether given (Continued)

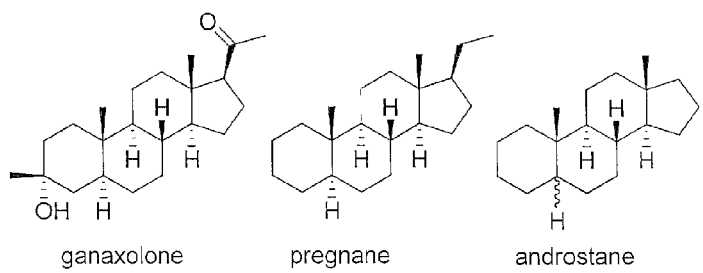

ganaxolone    pregnane    androstane earlier or later than 40-min (up to several hours) after organophosphate compound exposure. Neurosteroids are effective to attenuate long-term neuropsychiatric deficits caused by organophosphate exposure.

46 Claims, 17 Drawing Sheets

(56) References Cited

U.S. PATENT DOCUMENTS

| | | | | |
|---|---|---|---|---|
| 7,781,421 | B2 | 8/2010 | Covey et al. | 514/179 |
| 8,604,066 | B2 | 12/2013 | Baud et al. | 514/357 |
| 2013/0309306 | A1 | 11/2013 | Rogawski et al. | 424/489 |
| 2014/0050789 | A1 | 2/2014 | Rogawski et al. | 514/171 |
| 2014/0057885 | A1 | 2/2014 | Reddy et al. | 514/182 |

FOREIGN PATENT DOCUMENTS

| | | |
|---|---|---|
| WO | WO/1994/027608 | 12/1994 |
| WO | WO/1995/021617 | 8/1995 |
| WO | WO/1996/016076 | 5/1996 |
| WO | WO/1996/040043 | 12/1996 |
| WO | WO/1997/030731 | 8/1997 |
| WO | WO/2008/157460 | 12/2008 |
| WO | WO/2013/043985 | 3/2013 |
| WO | WO/2013/019711 | 4/2013 |
| WO | WO/2014/028398 | 2/2014 |
| WO | WO/2014/100231 | 6/2014 |

OTHER PUBLICATIONS

Apland, J. P. et al. (2010) "Higher susceptibility of the ventral versus the dorsal hippocampus and the posteroventral versus anterodorsal amygdala to soman-induced neuropathology," *Neurotoxicology* 31(5), 485-492.

Bajgar, J. (2004) "Organophosphates/nerve agent poisoning: mechanism of action, diagnosis, prophylaxis, and treatment," *Advances in Clinical Chemistry* 38, 151-216.

Bajgar, J. (2005) "Complex view on poisoning with nerve agents and organophosphates," *Acta Medica (Hradec Kralove)* 48(1), 3-21.

Balali-Mood, M. et al. (1998) "Treatment of organophosphate poisoning. Experience of nerve agents and acute pesticide poisoning on the effects of oximes," *Journal of Physiology-Paris* 92(5-6), 375-378.

Bali, A. et al. (2014) "Multifunctional aspects of allopregnanolone in stress and related disorders," *Progress in Neuro-Psychopharmacology and Biological Psychiatry* 48, 64-78.

Bandyopadhyaya, A. K. et al. (2010) "Neurosteroid Analogues. 15. A Comparative Study of the Anesthetic and GABAergic Actions of Alphaxalone, Δ(16)-Alphaxalone and Their Corresponding 17-Carbonitrile Analogues," *Bioorganic & Medicinal Chemistry Letters* 20(22), 6680-6684.

Banerjee, I. et al. (2014) "Efficacy of pralidoxime in organophosphorus poisoning: revisiting the controversy in Indian setting," *Journal of Postgraduate Medicine* 60(1), 27-30.

Benarroch, E. E. (2007) "Neurosteroids: endogenous modulators of neuronal excitability and plasticity," *Neurology* 68(12), 945-947.

Bialer, M. et al. (2013) "Progress report on new antiepileptic drugs: a summary of the Eleventh Eilat Conference (EILAT XI)," *Epilepsy Research* 103(1), 2-30.

Carver, C. M. et al. (2013) "Neurosteroid interactions with synaptic and extrasynaptic GABA(a) receptors: regulation of subunit plasticity, phasic and tonic inhibition, and neuronal network excitability," *Psychopharmacology* 230(2), 10.1007/s00213-00013-03276-00215.

Carver, C. M. et al. (2014) "Perimenstrual-Like Hormonal Regulation of Extrasynaptic δ-Containing GABA(A) Receptors Mediating Tonic Inhibition and Neurosteroid Sensitivity," *Journal of Neuroscience* 34(43), 14181-14197.

Costa, L. G. et al. (2005) "Measurement of paraoxonase (PON1) status as a potential biomarker of susceptibility to organophosphate toxicity," *Clinica Chimica Acta* 352(1), 37-47.

Coubard, S. et al. (2008) "Long-term consequences of soman poisoning in mice: Part 2. Emotional behavior," *Behavioural Brain Research* 191(1), 95-103.

Covey, D. F. et al. (2000) "Neurosteroid analogues. 8. Structure-activity studies of N-acylated 17a-aza-D-homosteroid analogues of the anesthetic steroids (3alpha, 5alpha)- and (3alpha,5beta)-3-hydroxypregnan-20-one," *Journal of Medicinal Chemistry* 43(17), 3201-3204.

De Araujo Furtado, M. et al. (2010) "Spontaneous recurrent seizures after status epilepticus induced by soman in Sprague-Dawley rats," *Epilepsia* 51(8), 1503-1510.

Deshpande, L. S. et al. (2010) "Development of a Prolonged Calcium Plateau in Hippocampal Neurons in Rats Surviving Status Epilepticus Induced by the Organophosphate Diisopropylfluorophosphate," *Toxicological Sciences* 116(2), 623-631.

Despain, K. E. et al. (2007) "The Toxicity of Soman in the African Green Monkey (*Chlorocebus aethiops*)," *Toxicology Mechanisms and Methods* 17(5), 255-264.

Dhir, A. et al. (2012) "Role of neurosteroids in the anticonvulsant activity of midazolam," *British Journal of Pharmacology* 165(8), 2684-2691.

Doctor, B. P. et al. (2005) "Bioscavengers for the protection of humans against organophosphate toxicity," *Chemico-Biological Interactions* 157-158, 167-171.

Dubrovsky, B. O. (2005) "Steroids, neuroactive steroids and neurosteroids in psychopathology," *Progress in Neuro-Psychopharmacology and Biological Psychiatry* 29(2), 169-192.

Eddleston, M. et al. (2008) "Management of acute organophosphorus pesticide poisoning," *Lancet* 371(9612), 597-607.

Engel, S. R. et al. (2001) "Neurosteroids and behavior," *International Review of Neurobiology* 46, 321-348.

Eskenazi, B. et al. (1999) "Exposures of children to organophosphate pesticides and their potential adverse health effects," *Environmental Health Perspectives* 107(Suppl 3), 409-419.

Flower, O. et al. (2012) "Sedation in Traumatic Brain Injury," *Emergency Medicine International*, 11.

Girdler, S. S. et al. (2007) "Neurosteroids in the context of stress: Implications for depressive disorders," *Pharmacology & Therapeutics* 116(1), 125-139.

Gunn, B. G. et al. (2015) "GABAA receptor-acting neurosteroids: A role in the development and regulation of the stress response," *Frontiers in Neuroendocrinology* 36, 28-48.

Han, M. et al. (1995) "Neurosteroid analogues. 3. The synthesis and electrophysiological evaluation of benz[e]indene congeners of neuroactive steroids having the 5 beta-configuration," *Journal of Medicinal Chemistry* 38(22), 4548-4556.

Han, M. et al. (1996) "Neurosteroid Analogues. 4. The Effect of Methyl Substitution at the C-5 and C-10 Positions of Neurosteroids on Electrophysiological Activity at GABBA Receptors," *Journal of Medicinal Chemistry* 39(21), 4218-4232.

Hogenkamp, D. J. et al. (2014) "Pharmacological profile of a 17beta-heteroaryl-substituted neuroactive steroid," *Psychopharmacology* 231(17), 3517-3524.

Hu, Y. et al. (1993) "Neurosteroid analogues: structure-activity studies of benz[e]indene modulators of GABAA receptor function. 1. The effect of 6-methyl substitution on the electrophysiological activity of 7-substituted benz[e]indene-3-carbonitriles," *Journal of Medicinal Chemistry* 36(24), 3956-3967.

Institute of Medicine (1996) *Veterans and Agent Orange*, The National Academies, http://www.ncbi.nlm.nih.gov/books/NBK232842/pdf/Bookshelf_NBK232842.pdf.

Jett, D. A. et al. (2010) "The CounterACT Research Network: Basic Mechanisms and Practical Applications," *Proceedings of the American Thoracic Society* 7(4), 254-256.

Jiang, X. et al. (2003) "Neurosteroid Analogues. 9. Conformationally Constrained Pregnanes Structure—Activity Studies of 13,24-Cyclo-18,21-dinorcholane Analogues of the GABA Modulatory and Anesthetic Steroids (3α,5α)- and (3α,5β)-3-Hydroxypregnan-20-one," *Journal of Medicinal Chemistry* 46(25), 5334-5348.

(56) References Cited

OTHER PUBLICATIONS

Jiang, X. et al. (2000) "A practical and facile route for the preparation of 18-norandrostan-17-ones from androstan-17-ones using SmI(2)-promoted cyclization and dehydroxylation," *Journal of Organic Chemistry* 65(11), 3555-3557.

Jokanović, M. et al. (2010) "Neurotoxic effects in patients poisoned with organophosphorus pesticides," *Environmental Toxicology and Pharmacology* 29(3), 195-201.

Jokanovic, M. et al. (2009) "Pyridinium oximes as cholinesterase reactivators. Structure-activity relationship and efficacy in the treatment of poisoning with organophosphorus compounds," *Current Medicinal Chemistry* 16(17), 2177-2188.

Joshi, S. et al. (2013) "GABAergic Transmission in Temporal Lobe Epilepsy: the Role of Neurosteroids," *Experimental Neurology* 244, 36-42.

Jurewicz, J. et al. (2008) "Prenatal and childhood exposure to pesticides and neurobehavioral development: review of epidemiological studies," *International Journal of Occupational Medicine and Environmental Health* 21(2), 121-132.

Katona, B. W. et al. (2008) "Neurosteroid analogues. 12. Potent enhancement of GABA-mediated chloride currents at GABAA receptors by ent-androgens," *European Journal of Medicinal Chemistry* 43(1), 107-113.

Kellinghaus, C. et al. (2012) "Treatment of status epilepticus in a large community hospital," *Epilepsy & Behavior* 23(3), 235-240.

King, S. R. (2008) "Emerging Roles for Neurosteroids in Sexual Behavior and Function," *Journal of Andrology* 29(5), 524-533.

Kokate, T. G. et al. (1994) "Anticonvulsant activity of neurosteroids: correlation with gamma-aminobutyric acid-evoked chloride current potentiation," *Journal of Pharmacology and Experimental Therapeutics* 270(3), 1223.

Kokate, T. G. et al. (1998) "Lack of anticonvulsant tolerance to the neuroactive steroid pregnanolone in mice," *Journal of Pharmacology and Experimental Therapeutics* 287(2), 553-558.

Lallement, G. et al. (1998) "Medical management of organophosphate-induced seizures," *Journal of Physiology—Paris* 92(5-6), 369-373.

Lan, N. C. et al. (1994) "Neuroactive Steroid Actions at the GABAA Receptor," *Hormones and Behavior* 28(4), 537-544.

Leibson, T. et al. (2008) "Organophosphate and carbamate poisoning: review of the current literature and summary of clinical and laboratory experience in southern Israel," *Israel Medical Association Journal* 10(11), 767-770.

Mayer, S. A. et al. (2002) "Refractory status epilepticus: Frequency, risk factors, and impact on outcome," *Archives of Neurology* 59(2), 205-210.

McDonough, J. H. et al. (2010) "Time-dependent reduction in the anticonvulsant effectiveness of diazepam against soman-induced seizures in guinea pigs," *Drug and Chemical Toxicology* 33(3), 279-283.

Mihalek, R. M. et al. (1999) "Attenuated sensitivity to neuroactive steroids in γ-aminobutyrate type A receptor delta subunit knockout mice," *Proceedings of the National Academy of Sciences* 96(22), 12905-12910.

Morrow, A. L. (2007) "Recent Developments in the Significance and Therapeutic Relevance of Neuroactive Steroids—Introduction to the Special Issue," *Pharmacology & Therapeutics* 116(1), 1-6.

Murata, K. et al. (1997) "Asymptomatic sequelae to acute sarin poisoning in the central and autonomic nervous system 6 months after the Tokyo subway attack," *Journal of Neurology* 244(10), 601-606.

Naylor, D. E. et al. (2005) "Trafficking of $GABA_A$ Receptors, Loss of Inhibition, and a Mechanism for Pharmacoresistance in Status Epilepticus," *Journal of Neuroscience* 25(34), 7724.

Nilsson, K. R. et al. (1998) "Neurosteroid Analogues. 6. The Synthesis and GABAA Receptor Pharmacology of Enantiomers of Dehydroepiandrosterone Sulfate, Pregnenolone Sulfate, and (3α,5β)-3-Hydroxypregnan-20-one Sulfate," *Journal of Medicinal Chemistry* 41(14), 2604-2613.

Nishiwaki, Y. et al. (2001) "Effects of sarin on the nervous system in rescue team staff members and police officers 3 years after the Tokyo subway sarin attack," *Environmental Health Perspectives* 109(11), 1169-1173.

Ohtani, T. et al. (2004) "Post-traumatic stress disorder symptoms in victims of Tokyo subway attack: a 5-year follow-up study," *Psychiatry and Clinical Neurosciences* 58(6), 624-629.

Okazaki, M. M. et al. (1995) "Hippocampal mossy fiber sprouting and synapse formation after status epilepticus in rats: Visualization after retrograde transport of biocytin," *Journal of Comparative Neurology* 352(4), 515-534.

Pandit, V. et al. (2011) "A case of organophosphate poisoning presenting with seizure and unavailable history of parenteral suicide attempt," *Journal of Emergencies, Trauma and Shock* 4(1), 132-134.

Paul, S. M. et al. (1992) "Neuroactive steroids," *FASEB Journal* 6(6), 2311-2322.

Peter, J. V. et al. (2006) "Oxime therapy and outcomes in human organophosphate poisoning: an evaluation using meta-analytic techniques," *Critical Care Medicine* 34(2), 502-510.

Prager, E. M. et al. (2014) "The recovery of acetylcholinesterase activity and the progression of neuropathological and pathophysiological alterations in the rat basolateral amygdala after soman-induced status epilepticus: Relation to anxiety-like behavior," *Neuropharmacology* 81, 64-74.

Rahimi, R. et al. (2006) "Increased morbidity and mortality in acute human organophosphate-poisoned patients treated by oximes: a meta-analysis of clinical trials," *Human & Experimental Toxicology* 25(3), 157-162.

Reddy, D. S. (2003) "Pharmacology of Endogenous Neuroactive Steroids," 15(3&4), 38.

Reddy, D. S. (2010) "Neurosteroids," *Progress in Brain Research* 186, 113-137.

Reddy, D. S. (2011) "Role of Anticonvulsant and Antiepileptogenic Neurosteroids in the Pathophysiology and Treatment of Epilepsy," *Frontiers in Endocrinology* 2(38).

Reddy, D. S. et al. (2004) "Anticonvulsant Activity of Progesterone and Neurosteroids in Progesterone Receptor Knockout Mice," *Journal of Pharmacology and Experimental Therapeutics* 310(1), 230.

Reddy, D. S. et al. (2013) "Experimental Models of Status Epilepticus and Neuronal Injury for Evaluation of Therapeutic Interventions," *International Journal of Molecular Sciences* 14(9), 18284-18318.

Reddy, D. S. et al. (2000) "Chronic Treatment with the Neuroactive Steroid Ganaxolone in the Rat Induces Anticonvulsant Tolerance to Diazepam but Not to Itself," *Journal of Pharmacology and Experimental Therapeutics* 295(3), 1241.

Reddy, D. S. et al. (2009) "Neurosteroid replacement therapy for catamenial epilepsy," *Neurotherapeutics* 6(2), 392-401.

Reddy, S. D. et al. (2015) "Midazolam as an anticonvulsant antidote for organophosphate intoxication—A pharmacotherapeutic appraisal," *Epilepsia* 56(6), 813-821.

Reddy, S. D. et al. (2015) "Antiseizure Activity of Midazolam in Mice Lacking δ-Subunit Extrasynaptic $GABA_A$ Receptors," *Journal of Pharmacology and Experimental Therapeutics* 353(3), 517.

Rogawski, M. A. et al. (2004) "Neurosteroids: endogenous modulators of seizure susceptibility," in *Epilepsy: Scientific Foundations of Clinical Practice* (Rho, J. M., et al., Eds.), pp. 319-355, Marcel Dekker, New York.

Romano, J. A. J. (2001) "Health Effects of Low-Level Exposure to Nerve Agents," in *Chemical Warfare Agents: Toxicity at Low Levels* (Somani, S. M., et al., Eds.), CRC Press, Boca Raton, FL.

Rosenbaum, C. et al. (2010) "Non-muscarinic therapeutic targets for acute organophosphorus poisoning," *Journal of Medical Toxicology* 6(4), 408-412.

Scaglione, J. B. et al. (2008) "Neurosteroid Analogues. 14. Alternative Ring System Scaffolds: GABA Modulatory and Anesthetic Actions of Cyclopenta[b]phenanthrenes and Cyclopenta[b]anthracenes," *Journal of Medicinal Chemistry* 51(5), 1309-1318.

Scaglione, J. B. et al. (2006) "Neurosteroid Analogues. 11. Alternative Ring System Scaffolds: δ-Aminobutyric Acid Receptor Modulation and Anesthetic Actions of Benz[f]indenes," *Journal of Medicinal Chemistry* 49(15), 4595-4605.

(56) References Cited

OTHER PUBLICATIONS

Shrot, S. et al. (2014) "Prevention of organophosphate-induced chronic epilepsy by early benzodiazepine treatment," *Toxicology* 323(0), 19-25.

Srivastava, D. P. et al. (2011) "Rapid Estrogen Signaling in the Brain: Implications for the Fine-Tuning of Neuronal Circuitry," *Journal of Neuroscience* 31(45), 16056.

US EPA Office of Pesticide Programs. (2011) Organophosphorous Cumulative Risk Assessment 2006 Update, (EPA, Ed.).

Usami, N. et al. (2002) "Substrate Specificity of Human 3(20)α-Hydroxy steroid Dehydrogenase for Neurosteroids and Its Inhibition by Benzodiazepines," *Biological and Pharmaceutical Bulletin* 25(4), 441-445.

Vallée, M. et al. (2001) "Neurosteroids in learning and memory processes," in *International Review of Neurobiology*, pp. 273-320, Academic Press.

Venkatesh, S. et al. (2006) "Progression of type I to type II paralysis in acute organophosphorous poisoning: is oxidative stress significant?," *Archives of Toxicology* 80(6), 354-361.

Walker, C. H. (2001) in *Organic Pollutants: An Ecotoxicological Perspective*, pp. 186-193, Taylor & Francis.

Wang, C. et al. (2007) "Neurosteroid Analogues. 13. Synthetic methods for the preparation of 2β-hydroxygonane derivatives as structural mimics of ent-3α-hydroxy steroid modulators of GABA(A) receptors," *Tetrahedron* 63(33), 7977-7984.

Wasterlain, C. G. et al. (2009) "Molecular basis of self-sustaining seizures and pharmacoresistance during status epilepticus: The receptor trafficking hypothesis revisited," *Epilepsia* 50, 16-18.

Wohlfarth, K. M. et al. (2002) "Enhanced Neurosteroid Potentiation of Ternary $GABA_A$ Receptors Containing the δ Subunit," *Journal of Neuroscience* 22(5), 1541.

Worek, F. et al. (2005) "Diagnostic aspects of organophosphate poisoning," *Toxicology* 214(3), 182-189.

Yanagisawa, N. et al. (2006) "Sarin experiences in Japan: Acute toxicity and long-term effects," *Journal of the Neurological Sciences* 249(1), 76-85.

Yurumez, Y. et al. (2007) "Acute Organophosphate Poisoning in University Hospital Emergency Room Patients," *Internal Medicine* 46(13), 965-969.

Zeng, C.-m. et al. (2005) "Neurosteroid Analogues. 10. The Effect of Methyl Group Substitution at the C-6 and C-7 Positions on the GABA Modulatory and Anesthetic Actions of (3α,5α)- and (3α,5β)-3-Hydroxypregnan-20-one," *Journal of Medicinal Chemistry* 48(8), 3051-3059.

Zeng, C. et al. (2000) "Neurosteroid analogues. 7. A synthetic route for the conversion of 5 beta-methyl-3-ketosteroids into 7(S)-methyl-substituted analogues of neuroactive benz[e]indenes," *Journal of Organic Chemistry* 65(7), 2264-2266.

Zhan, R.-Z. et al. (2009) "Enhanced Tonic GABA Current in Normotopic and Hilar Ectopic Dentate Granule Cells After Pilocarpine-Induced Status Epilepticus," *Journal of Neurophysiology* 102(2), 670.

Zoltani. (2002) "Organophosphate Caused Cardia Toxicity: Action Potential Dynamics in Atrial Tissue," *Army Research Laboratory*, 1-15.

Figure 10

(A) Epileptogenic events (B)

(C) Memory deficits

NORT

Habituation
↓
Sample phase
↓
Testing phase

METHOD OF TREATING ORGANOPHOSPHATE INTOXICATION BY ADMINISTRATION OF NEUROSTEROIDS

STATEMENT OF GOVERNMENT SUPPORT

This invention was made with governmental support under Grant Nos NS076426 and NS083460 awarded by the National Institutes of Health. The government has certain rights in the invention.

FIELD OF THE INVENTION

The present invention is related to the field of organophosphate intoxication. Compositions and methods are disclosed that provide an effective post-exposure treatment of organophosphate intoxication. Such treatment not only reverses organophosphate intoxication more effectively than benzodiazepines but prevents subsequent neuronal injury and long-term neuropsychiatric deficits. For example, neurosteroid compounds either alone, or in combination with conventional organophosphate antidotes including, but not limited to, atropine and/or pralidoxime are provided.

BACKGROUND

The development of organophosphate chemistry and associated biological effects resulted from the use of chemical warfare agents produced during World War II. These compounds can adversely affect the human nervous system even at low levels of exposure. For example, fruits and vegetables that are commonly eaten by children, including peaches, apples, grapes, green beans, and pears, are among the foods most commonly contaminated with organophosphates. Children can also be exposed to organophosphate compounds through the air, food, dust and soil, and even pets. Children of farmworkers and children in agricultural areas are among the most exposed to organaphosphate compounds, although urban children are also at risk.

Since the advent of chemical warfare during World War II, organophosphorous compounds have become widely available as pest-control agents. Became of their relatively low cost and ability to be applied on a wide range of larger insects and crops, organophosphate compounds have become the most widely used class of insecticides in the United States. Organphosphates are also among the most common active ingredients in pesticide poisonings.

What is needed in the art are compositions capable of being administered as clinically effective, delayed, treatments for non-lethal and potentially lethal organophosphate exposure, using conventional administration devices, such that the associated conditions of cholinergic crises and non-cholinergic crises are controlled and/or averted. Such a treatment method provides an effective on-scene treatment of an exposed subject by non-medical personnel in military settings and healthcare first responders in civilian incidents, and also provides a sufficient treatment window to allow transport of an exposed subject to a medical facility for effective treatment. In cases of mass casualties, this can be done by first responders most conveniently by means of antoinjectors containing an effective medication.

SUMMARY OF THE INVENTION

The present invention is related to the field of organophosphate intoxication. Compositions and methods are disclosed that provide an effective post-exposure treatment of organophosphate intoxication. Such treatment not only reverses organophosphate intoxication more effectively than benzodiazepines but prevents subsequent neuronal injury and long-term neuropsychiatry deficits. For example, neurosteroid compounds either alone, or in combination with conventional organophosphate antidotes including, but not limited to, atropine and/or pralidoxime are provided.

In one embodiment, the present invention contemplates a method comprising: a) providing; i) a subject exhibiting a cholinergic crisis subsequent to an organophosphate compound exposure; and ii) a composition comprising a neurosteroid and a pharmaceutical carrier; and b) administering said composition to said subject under conditions such that said cholinergic crisis is reduced. In one embodiment, the composition consists of a neuosteroid and a pharmaceutical carrier. In one embodiment, the composition is administered less than forty (40) minutes after said organophosphate compound exposure. In one embodiment, the composition is administered at forty (40) minutes or later after said organophosphate compound exposure. In one embodiment, the composition is administered between forty (40) minutes and two (2) hours after said organophosphate compound exposure. In one embodiment, the composition is administered between forty (40) minutes and two (2) hours after said organophosphate compound exposure. In one embodiment, the composition is administered less than sixty (60) minutes later after a benzodiazepine administered at forty (40) minutes or later after said organophosphate compound exposure. In one embodiment, the pharmaceutical composition has an improved effectiveness to reduce said cholinergic crisis than benzodiazepine agents selected from the group consists of midazolam, diazepam and lorazepam. In one embodiment, the cholinergic crisis comprises bradycardia, hypotension, bronchorrhoea, salivation, emesis, diarrhea, abdominal pain, urinary frequency, and cardiac rhythm disturbance. In one embodiment, the cholinergic crisis comprises muscular weakness, muscular paralysis, respiratory insufficiency, and pallor perspiration. In one embodiment, the cholinergic crisis comprises consciousness alteration, hallucinations, seizures, respiratory center inhibition and skeletal muscle paralysis. In one embodiment, the cholinergic crisis comprises type II paralysis. In one embodiment, the organophosphate compound is a nerve agent. In one embodiment, the organophosphate compound is a pesticide. In one embodiment, the neurosteroid is ganaxolone. In one embodiment, the neurosteroid includes, but is not limited to, pregnanolone, allopregnanolone, allotetahydrodeoxycorticosterone (THDOC), alfoxolone, androstanediol, and related neurosteroidal agents thereof. In one embodiment, the nerve agent is soman. In one embodiment, the nerve agent includes, but is not limited to O-ethyl S-[2-(diisopropylamino) ethyl] methylphosphonothioate) (VX), and related chemical agents thereof. In one embodiment, the pesticide is diisopropyl-fluorophosphate. In one embodiment, the administering is selected from the group consisting of parenteral, intramuscular, subcutaneous, intravenous, inhalation, percutaneous, rectal, buccal and oral administration.

In one embodiment, the present invention contemplates a method comprising; a) providing; i) a subject exhibiting a cholinergic crisis subsequent to an organophosphate compound exposure; and ii) a pharmaceutical composition comprising a neurosteroid and an organophosphate antidote selected from the group consisting of atropine and pralidoxime; and b) administering said pharmaceutical composition to said subject under conditions such that said cholinergic crisis is reduced. In one embodiment, the pharmaceutical composition consists of said neurosteroid and said organophosphate antidote selected from the group consisting of atropine and pralidoxime. In one embodiment, the pharmaceutical composition is administered less than forty (40) minutes after said organophosphate compound exposure. In one embodiment, the composition is administered at forty (40) minutes or later after said organophosphate compound exposure. In one embodiment, the composition is administered between forty (40) minutes and two (2) hours after said organophosphate compound exposure. In one embodiment, the composition is administered less than sixty (60) minutes later after a benzodiazepine administered at forty (40) minutes or later after said organophosphate compound exposure. In one embodiment, the pharmaceutical composition has an improved clinical effectiveness to reduce the cholinergic crisis than benzodiazepine agents, selected from the group consists of midazolam, diazepam and lorazepam. In one embodiment, the cholinergic crisis comprises bradycardia, hypotension, bronchorrhoea, salivation, emesis, diarrhea, abdominal pain, urinary frequency, and cardiac rhythm disturbance. In one embodiment, the cholinergic crisis comprises muscular weakness, muscular paralysis, respiratory insufficiency, and pallor perspiration. In one embodiment, the cholinergic crisis comprises consciousness alteration, hallucinations seizures, respiratory center inhibition and skeletal muscle paralysis. In one embodiment, the cholinergic crisis comprises type II paralysis. In one embodiment, the organophosphate compound is a nerve agent. In one embodiment, the organophosphate compound is a pesticide. In one embodiment, the neurosteroid is ganaxolone. In one embodiment, the neurosteroid includes, but is not limited to, pregnanolone, allopregnanolone, allotetrahydrodeoxycorticosterone (THDOC), alfaxolone, androstanediol, and related neurosteroidal agents thereof. In one embodiment, the nerve agent is soman. In one embodiment, the nerve agent includes, but is not limited to O-ethyl S-[2-(diisopropylamino) ethyl] methylphosphonothioate) (VX), and related chemical agents thereof. In one embodiment, the pesticide is diisopropyl-fluorophosphate. In one embodiment, the administering is selected from the group consisting of parenteral, intramuscular, subcutaneous, intravenous, inhalation, percutaneous, rectal, buccal and oral administration.

In one embodiment, the present invention contemplates a method comprising: a) providing; i) a subject exhibiting at least one symptom of a non-cholinergic crisis subsequent to an organophosphate compound exposure; and ii) a composition comprising a neurosteroid and a pharmaceutical carrier; and b) administering said composition to said subject under conditions such that said at least one symptom of said non-cholinergic crisis is reduced. In one embodiment, the composition consists of said neurosteroid and said pharmaceutical carrier. In one embodiment, the composition is administered less than forty (40) minutes after said organophosphate compound exposure. In one embodiment, the composition is administered at forty (40) minutes or later after said organophosphate compound exposure. In one embodiment, the composition is administered between forty (40) minutes and two (2) hours after said organophosphate compound exposure. In one embodiment, the composition is administered less than sixty (60) minutes later after a benzodiazepine administered at forty (40) minutes or later after said organophosphate compound exposure. In one embodiment, the pharmaceutical composition has an improved effectiveness to reduce the non-cholinergic crisis than benzodiazepine agents selected from the group consists of midazolam, diazepam and lorazepam. In one embodiment, the at least one symptom of the non-cholinergic crisis comprises a benzodiazepine-refractory intoxication symptom. In one embodiment, the at least one symptom of the non-cholinergic crisis includes, but is not limited to, cerebral edema, blood barrier dysfunction, neural inflammation, non-neural inflammation, neuronal cell apoptosis, neuronal cell necrosis, neuronal cell injury, neuronal cell death, neuronal cell loss, axonal degeneration, axonal sprouting and neurodegeneration. In one embodiment, the at least one symptom of the non-cholinergic crisis includes, but is not limited to, subacute behavioral dysfunction, subacute neurological dysfunction, individual neuropsychiatric disorders and clustered neuropsychiatric disorders. In one embodiment, the organophosphate compound is a nerve agent. In one embodiment, the organophosphate compound is a pesticide. In one embodiment, the neurosteroid is ganaxolone. In one embodiment, the neurosteroid is ganaxolone. In one embodiment, the neurosteroid includes, but is not limited to, pregnanolone, allopregnanolone, allotetrahydrodeoxycorticosterone (THDOC), alfaxolone, androstanediol, and related neurosteroidal agents thereof. In one embodiment the nerve agent is soman. In one embodiment, the nerve agent includes, but is not limited to, O-ethyl S-[2-(diisopropylamino) ethyl] methyl phosphonothioate) (VX), and related chemical agents thereof. In one embodiment, the pesticide is diisopropyl-fluorophosphate. In one embodiment, the administering is selected from the group consisting of parenteral, intramuscular, subcutaneous, intravenous, inhalation, percutaneous, rectal, buccal and oral administration.

In one embodiment, the present invention contemplates a method for treating organophosphate intoxication in a subject in need thereof, comprising administering a therapeutically effective amount of a neurosteroidal compound. In one embodiment, the treating comprises reversing organophosphate intoxication. In one embodiment, the neurosteroidal compound is selected from the group including, but not limited to, pregnane, androstane, 19-norandrostanes, and norpregnane and derivatives thereof. In one embodiment, the neurosteroidal compound includes, but is not limited to, ganaxolone, pregnanolone, and androstanediol and their analogs, salts and prodrugs. In one embodiment, the administering further comprises a standard nerve agent antidote selected from the group consisting of atropine and pralidoxime. In one embodiment, the administering is earlier than forty (40) minutes after exposure to said organophosphate. In one embodiment, the administering is greater than forty (40) minutes after exposure to said organophosphate. In one embodiment, the administering is less than two (20) hours after exposure to said organophosphate. In one embodiment, the composition is administered less than sixty (60) minutes later after a benzodiazepine administered at forty (40) minutes or later after said organophosphate compound exposure. In one embodiment, the said pharmaceutical composition has an improved effectiveness to treat the organophosphate intoxication than benzodiazepine agents selected from the group consists of midazolam, diazepam and lorazepam. In one embodiment, the neurosteroidal compound is formulated with a pharmaceutical carrier. In one embodiment, the pharmaceutical carrier is a parenteral pharmaceutical carrier. In one embodiment, the administering is intrapulmonary. In one embodiment, the subject exhibits cluster symptoms of organophosphate chemical intoxication. In one embodiment, the subject exhibits at least one symptom of organophosphate intoxication including, but not limited to, a cluster symptom, delayed intoxication, benzodiazepine-refractory intoxication, hyperactivity, excitability, hyperexcitability, synchronous, activity and CNS signs and symptoms of intoxication or cholinergic hyperactivation.

In one embodiment, the present invention contemplates a method comprising: a) providing; i) a subject exhibiting a cholinergic crisis subsequent to an organophosphate compound exposure; and ii) a pharmaceutical composition comprising a neurosteroid and a benzodiazepine adjunct selected from the group consisting of midazolam, diazepam and lorazepam; and b) administering said pharmaceutical composition to said subject under conditions such that said cholinergic crisis is reduced. In one embodiment, the pharmaceutical composition consists of said neurosteroid and said organophosphate antidote selected from the group consisting of atropine and pralidoxime. In one embodiment, the pharmaceutical composition is administered less than forty (40) minutes after said organophosphate compound exposure. In one embodiment, the said composition is administered at forty (40) minutes or later after said organophosphate compound exposure. In one embodiment, the composition is administered between forty (40) minutes and two (2) hours after said organophosphate compound exposure. In one embodiment, the composition is administered less than sixty (60) minutes later after a benzodiazepine administered at forty (40) minutes or later after said organophosphate compound exposure. In one embodiment, the pharmaceutical composition has an improved effectiveness to reduce the cholinergic crisis than benzodiazepine agents selected from the group consists of midazolam and diazepam. In one embodiment, the cholinergic crisis comprises bradycardia, hypotension, bronchorrhoea, salivation, emesis, diarrhea, abdominal pain, urinary frequency, and cardiac rhythm disturbance. In one embodiment, the cholinergic crisis comprises muscular weakness, muscular paralysis, respiratory insufficiency, and pallor perspiration. In one embodiment, the cholinergic crisis comprises consciousness alteration, hallucinations, seizures, respiratory center inhibition and skeletal muscle paralysis. In one embodiment, the cholinergic crisis comprises type II paralysis. In one embodiment, the organophosphate compound is a nerve agent. In one embodiment, the organophosphate compound is a pesticide. In one embodiment, the neurosteroid is ganaxolone. In one embodiment, the neurosteroid is ganaxolone. In one embodiment, the neurosteroid comprises of pregnanolone, allopregnanolone, allotetrahydrodeoxycorticosterone (THDOC), alfaxolone, androstanediol, and related neurosteroidal agents thereof. In one embodiment, the nerve agent is soman. In one embodiment, the nerve agent includes, but is not limited to, O-ethyl S-[2-(diisopropylamino) ethyl] methylphosphonothioate (VX), and related chemical agents thereof. In one embodiment, the pesticide is diisopropyl-fluorophosphate. In one embodiment, the administering is selected from the group consisting of parenteral, intramuscular, subcutaneous, intravenous, inhalation, percutaneous, rectal, buccal and oral administration.

In one embodiment, the present invention contemplates a method comprising: a) providing; i) a subject exhibiting at least one late-onset or long-term neuropsychiatric symptom of a cholinergic or non-cholinergic crisis subsequent to an organophosphate compound exposure; and ii) a composition comprising a neurosteroid and a pharmaceutical carrier; and b) administering said composition to said subject under conditions such that said at least one late-onset or long-term neuropsychiatry symptom of said cholinergic or non-cholinergic crisis is reduced. In one embodiment, the composition consists of said neurosteroid and said pharmaceutical carrier. In one embodiment, the composition is administered less than forty (40) minutes after said organophosphate compound exposure. In one embodiment, the composition is administered at forty (40) minutes or later after said organophosphate compound exposure. In one embodiment, the composition is administered between forty (40) minutes and two (2) hours after said organophosphate compound exposure. In one embodiment, the composition is administered less than sixty (60) minutes later after a benzodiazepine administered at forty (40) minutes or later after said organophosphate compound exposure. In one embodiment, the pharmaceutical composition has an improved effectiveness to reduce the non-cholinergic crisis than benzodiazepine agents selected from the group consists of midazolam, diazepam and lorazepam. In one embodiment, the at least one late-onset symptom of said cholinergic or non-cholinergic crisis includes, but is not limited to, chronic behavioral dysfunction, neurological deficit, cognitive dysfunction, epileptogenic manifestation, and/or mossy fiber sprouting. In one embodiment, the at least one late-onset or long-term neuropsychiatric symptom of the non-cholinergic crisis includes, but is not limited to, cerebral edema, blood barrier dysfunction, neural inflammation, non-neural inflammation, neuronal cell apoptosis, neuronal cell necrosis, neuronal cell injury, neuronal cell death, neuronal cell loss, axonal degeneration, axonal sprouting and/or neurodegeneration. In one embodiment, the at least one late-onset symptom or late-onset non-cholinergic crisis includes, but is not limited to, behavioral dysfunction, neurological dysfunction, individual neuropsychiatric disorders, and/or clustered neuropsychiatric disorders. In one embodiment, the organophosphate compound is a nerve agent. In one embodiment, the organophosphate compound is a pesticide. In one embodiment, the neurosteroid is ganaxolone. In one embodiment, the neurosteroid includes, but is not limited to, pregnanolone, allopregnanolone, allotetrahydrodeoxycorticosterone (THDOC), alfaxolone, androstanediol, and related neurosteroidal agents thereof. In one embodiment, the nerve agent is soman. In one embodiment, the nerve agent includes, but is not limited, to O-ethyl S-[2-(diisopropylamino) ethyl] methylphosphonothioate) (VX), and related chemical agents thereof. In one embodiment, the pesticide is diisopropyl-fluorophosphate. In one embodiment, the administering is selected from the group consisting of parenteral, intramuscular, subcutaneous, intravenous, inhalation, percutaneous, rectal, buccal and oral administration.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity but also plural entities and also includes the general class of which a specific example may be used for illustration. The terminology herein is used to describe specific embodiments of the invention, but their usage does not delimit the invention, except as outlined in the claims.

The term "about" as used herein, in the context of any of any assay measurements refers to +/−5% of a given measurement.

The term "organophosphate compounds" as used herein, refers to any compounds have structural features comprising a terminal oxygen connected to phosphorus by a double bond, i.e. a phosphoryl group; two lipophilic groups bonded to the phosphorus; and a leaving group bonded to the phosphorus, often a halide. For example, such organophosphate compounds are nerve agents including, but are not limited to, tabun, sarin, soman (GD), GF, VR and/or VX. Alternatively, such organophosphate compounds are pesticides including, but not limited to, diisopropyl-fluorophosphate, azinphos-methyl, chlorpyrifos, diazinon, dichlorvos, dimethoate, ethephon, malathion, methamidophos, naled, and/or oxydemeton-methyl.

The terms "neuroactive steroid" or "neurosteroids" interchangeably refer to steroids that rapidly alter neuronal excitability through interaction with neurotransmitter-gated ion channels, specifically $GABA_A$ receptors. Exemplary neuroactive steroids include without limitation alphaxolone, alphadolone, hydroxydione and minaxolone. The neuroactive steroid ganaxolone finds use for the treatment of epilepsy. Illustrative endogenous neuroactive steroids, e.g., allopregnanolone and tetrahydrodeoxycorticosterone find use in various embodiments described herein. In some embodiments, the neurosteroid is selected from the group consisting of allopregnanolone, allotetrahydro-deoxycorticosterone, ganaxolone, alphaxolone, alphadolone, androstanediol (5α-androstan-3α,17β-diol), androsterone (5α-androstan-3α-ol-17-one), etiacholanone (5β-androstan-3α-ol-17-one), hydroxydione, minaxolone, and Althesin. Other neurosteroids of use include without limitation allotetrahydrodeoxycorticosterone (3α,21-dihydroxy5α-pregnan-20-one; THDOC), 3α21-dihydroxy-5β-pregnan-20-one, pregnanolone (3α-hydroxy-5β-pregnan-20-one), ganaxolone (INN, also known as CCD-1042; IUPAC name (3α,5α)-3α-hydroxy-3β-methyl-pregnan-20-one; 1-[(3R, 5S,8R,9S, 1OS, 13S, 14S,17S)-3-hydroxy-3, 10, 13-trimethyl 1,2,4,5, 6,7,8,9,11,12,14,15,16,17-tetradecahydrocyclopenta [a]phenanthren-17-yl]ethanone), alphaxolone, alphadolone, hydroxydione, minaxolone, and Althesin (a mixture of alphaxolone, alphadolone, tetrahydrodeoxycorticosterone, pregnenolone, dehydroepiandrosterone (DHEA), 7-substituted benz[e]indene-3-carbonitriles (see, e.g., Hu, et al., J Med. Chem. (1993) 36 (24):3956-67); 7-(2-hydroxyethyl) benz[e]indene analogues (see, e.g., Han, et al., J Med. Chem. (1995) 38 (22):4548-56); 3alpha-hydroxy-5alpha-pregnan20-one and 3alpha-hydroxy-5beta-pregnan-20-one analogues (see, e.g., Han, et al., J Med. Chem. (1996) 39 (21): 4218-32); enantiomers of dehydroepiandrosterone sulfate, pregnenolone sulfate, and (3alpha,5beta)-3-hydroxypregnan-20-one sulfate (see, e.g., Nilsson, et al., J Med. Chem. (1998) 41 (14):2604-13); 13,24-cyclo-18,21-dinorcholane analogues (see, e.g., Jiang, et al., J Med. Chem. (2003) 46 (25):5334-48); N-acylated 17a-aza-D-homosteroid analogues (see, e.g., Covey, et al., J Med. Chem. (2000) 43 (17): 3201-4); 5 beta-methyl-3-ketosteroid analogues (see, e.g., Zeng, et al., J Org. Chem. (2000) 65 (7):2264-6); 18-norandrostan-17-one analogues (see, e.g., Jiang, et al.; J Org. Chem. (2000) 65 (11):3555-7); (3alpha,5alpha)- and (3alpha, 5beta)-3-hydroxypregnan-20-one analogs (see, e.g., Zeng, et al., J Med. Chem. (2005) 48 (8):3051-9); benz[f] indenes (see, e.g., Scaglione, et al., J Med. Chem. (2006) 49 (15):4595605); enantiomers of androgens (see, e.g., Katona, et al., Eur J Med. Chem. (2008) 43 (1):107-13); cyclopenta [b]phenanthrenes and cyclopenta[b]anthracenes (see, e.g., Scaglione, et al., J Med. Chem. (2008) 51 (5):1309-18); 2beta-hydroxygonane derivatives (see, e.g., Wang, et al., Tetrahedron (2007) 63 (33):7977-7984); Δ16-alphaxalone and corresponding 17-carbonitrile analogues (see, e.g., Bandyopadhyaya, et al., Bioorg Med Chem. Lett. (2010) 20 (22):6680-4); Δ(16) and Δ(17(20)) analogues of Δ(16)-alphaxalone (see, e.g., Stastna, et al., J Med. Chem. (2011) 54 (11):3926-34); neurosteroid analogs developed by CoCensys (now Purdue Neuroscience) (e.g., CCD-3693, C02-6749 (a.k.a., GMA-839 and WAY141839); neurosteroid analogs described in U.S. Pat. No. 7,781,421 and in PCT Patent Publications WO 2008/157460; WO 1993/003732; WO 1993/018053; WO 1994/027608; WO 1995/021617; WO 1996/016076; WO 1996/040043, as well as salts, hemisuccinates, nitrosylated, sulfates and derivatives thereof; neurosteroid analogs described International Published Application WO 2013/019711 and Hogenkamp et al., "Pharmacological profile of a 17β-heteroaryl-substituted neuroactive steroid" Psychopharmacology 231; 3517-3524 (2014).

The term "benzodiazepine-refractory intoxication' as used herein refers to any subject previously treated for organophosphate intoxication with a benzodiazepine, manifests symptoms of neuronal injury, neuronal loss, neurodegeneration, axonal degeneration, blood-brain barrier dysfunction, and/or neuroinflammation.

The term "organophosphate antidote" as used herein, refers to any conventionally used and accepted compound to treat organophosphate intoxication that is approved by the United States Food and Drug Administration.

The term "cholinergic crisis" as used herein, refers to a set of immediate and short-term symptoms resulting from an overactivity of cholinergic neurons. Such a set of symptoms is typically seen subsequent to the exposure of a subject to an organophosphate compound. Generally, symptoms of a cholinergic crisis are evident when a biologically active concentration of an organophosphate compound is present in a subject.

The term "non-cholinergic crisis" as used herein, refers to a set of progressive and long-term symptoms resulting from generalized neuronal damage induced by a cholinergic crisis. Such a set of symptoms is typically seen subsequent to the exposure of a subject to an organophosphate compound. Generally, symptoms of a non-cholinergic crisis are evident when a biologically active concentration of an organophosphate compound is not present in a subject.

The term "effective amount" as used herein, refers to a particular amount of a pharmaceutical composition comprising a therapeutic agent that achieves a clinically beneficial result (i.e., for example, a reduction of symptoms). Toxicity and therapeutic efficacy of such compositions can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The term "symptom", as used herein, refers to any subjective or objective evidence of disease or physical disturbance observed by the patient. For example, subjective evidence is usually based upon patient self-reporting and may include, but is not limited to, pain, headache, visual disturbances, nausea and/or vomiting. Alternatively, objective evidence is usually a result of medical testing including, but not limited to, body temperature, complete blood count, lipid panels, thyroid panels, blood pressure, heart rate, electrocardiogram, tissue and/or body imaging scans.

The terms "reduce," "inhibit," "diminish," "suppress," "decrease," "attenuate," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "injury" as used herein, denotes a bodily disruption of the normal integrity of tissue structures. In one sense, the term is intended to encompass irritation, inflammation, infection, and the development of fibrosis. In another sense, the term is intended to encompass injury induced by biochemical responses to chemical toxicity and/or causticity.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering", as used herein, refers to any method of providing a composition to a patient such that the composition has its intended effect on the patient. An exemplary method of administering is by a direct mechanism such as, parenteral intravenous, intramuscular, subcutaneous, oral etc.

The term "patient" or "subject", as used herein, is a human or animal and need not be hospitalized. For example, out-patients, persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term, "pharmaceutically acceptable carrier", as used herein, includes any and all solvents, or a dispersion medium including, but not limited to, water, cyclodextrin, ethanol, polyol (for example, glycerol, propylene glycol, and liquid polyethylene glycol, and the like), suitable mixtures thereof, and vegetable oils, coatings, isotonic and absorption delaying agents, liposome, commercially available cleansers, solubility enhancers (for example, cyclodextrins) and the like. Supplementary bioactive ingredients also can be incorporated into such carriers.

The term "biologically active" refers to any molecule having structural, regulatory or biochemical functions. For example, biological activity may be determined, for example, by measuring changes in a biochemical and/or physiological pathway as a result of the presence of the molecule.

The term "pesticide" refers to compounds having the structural features of organophosphate or non-organophosphate that can destroy or exterminate pests and related organisms and that act via cholinergic and non-cholinergic modes of action. For example, organophosphate pesticides include, but limited to, acephate, azinophosmethyl, bensulide, bomyl, bromophos, dichlorvos, ethion, disulfoton, parathion, fenophosphon, fonofos, mathion, monocrotophos, phenthoate, DFP, phosphamidon, propetamphos, quinalphos, tetrachlorvinphos, tetraethyl pyrophosphate and trichlorfon.

The term "benzodiazepine" refers to compounds having the structural features of benzodiazepine and that activates brain GABA-A receptors at the benzodiazepine recognition sites for producing calming effects. Benzodiazepines are drugs that have been used as CNS depressants and used to induce mild sedation and sleep; and used as an anxiolytic, hypnotic, anticonvulsant, and anesthetic adjunct. Exemplary benzodiazepines include without limitation bretazenil, clonazepam, cloxazolam, clorazepate, diazepam, fludiazepam, flutoprazepam, lorazepam, midazolam, nimetazepam, nitrazepam, phenazepam, temazepam and clobazam.

The term "cyclodextrin" refers to pharmaceutical additives used in formulation of active medications as mixtures, admixtures, solutions or suspensions for administration of medication products for parenteral, oral, percutaneous or inhalation administration. Cyclodextrins include, but not limited to, α-cyclodextrin, β-cyclodextrin or a γ-cyclodextrin or their analogs consisting of hydroxypropyl-β-cyclodextrin, endotoxin controlled β-cyclodextrin sulfobutyl ethers, a sulfo butyl ether β-cyclodextrin (e.g., CAPTISOL®) or cyclodextrin sodium salts.

(A) Bright-field images show NeuN-positive principal neurons within the hippocampus subfields CA1, CA3 and dentate hilus. (B) Absolute quantification of NeuN-positive principal neurons in the hippocampus subfields by unbiased neurostereology. (C) The extend of neuroprotection of NeuN (+) principal neurons by ganaxolone treatment at 40, 60 and 120 min after soman exposure as compared to untreated soman control group. (D) Bright-field images snow parvalbumin (PV)-positive GABAergic inhibitory interneurons within the hippocampus subfield CA1, CA3 and dentate hilus. (E) Absolute quantification of PV-positive interneurons in the hippocampus subfields by unbiased neurostereology. (F) The extent of neuroprotection of PV(+) interneurons by ganaxolone treatment at 40, 60 and 120 min after soman exposure as compared to untreated soman control group. Data represent mean±SEM (N=4-7 rats per group).

Figure 6:
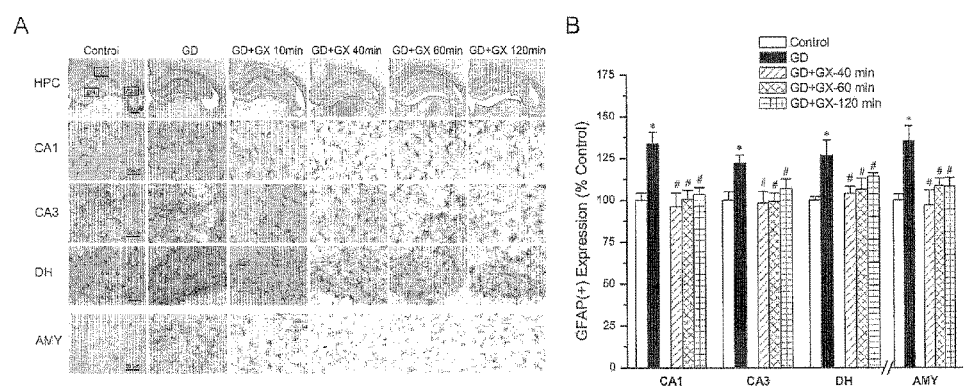

FIG. 6A-B presents exemplary data showing protective activity of delayed ganaxolone treatment (10 mg/kg, IM) against soman-induced neuroinflammation in rats. (A) Time-course profile of protective profile of ganaxolone treatment on astrocytic inflammation response 24 h following soman exposure. Bright-field images show glial fibrillary acidic protein (GFAP)-positive staining within the hippocampus subfields and amygdala. (B) Quantification of GFAP-positive immunostaining in the hippocampus subfields and amygdala by area fraction approach. The extent of protection of GFAP(+) upregulation by ganaxolone treatment at 40, 60 and 120 min after soman exposure is compared to an untreated soman control group. Data represent mean±SEM (N=4-6 rats per group). *P<0.01 as compared to control group as determined by one-way ANOVA with post hoc student's t-test.

FIG. 7A-C presents exemplary data showing efficacy of delayed treatment with neurosteroids allopregnanolone (10 mg/kg, IM), THDOC (10 mg/kg, IM), alfaxolone (10 mg/kg, IM) and androstanediol (100 mg/kg, IM) against the nerve agent soman-induced OP intoxication, seizures and status epilepticus. (A) Time-course behavioral profile of protective activity of neurosteroids against OP intoxication caused by soman exposure in rats. (B) Time-course EEG profile of protective activity of neurosteroids against OP intoxication caused by soman exposure in rats. (C) Latency for termination of soman-induced seizures or status epilepticus by neurosteroids treatment in rats. Neurosteroids were given at 40 min after soman exposure and behavioral stages and EEG seizure activity were monitored continuously for 24 h. Data presented as mean or mean±SEM (n=7 to 12 rats in each group). *P<0.01 as compared to control group as determined by one-way ANOVA with post hoc student's t-test.

Figure 8:
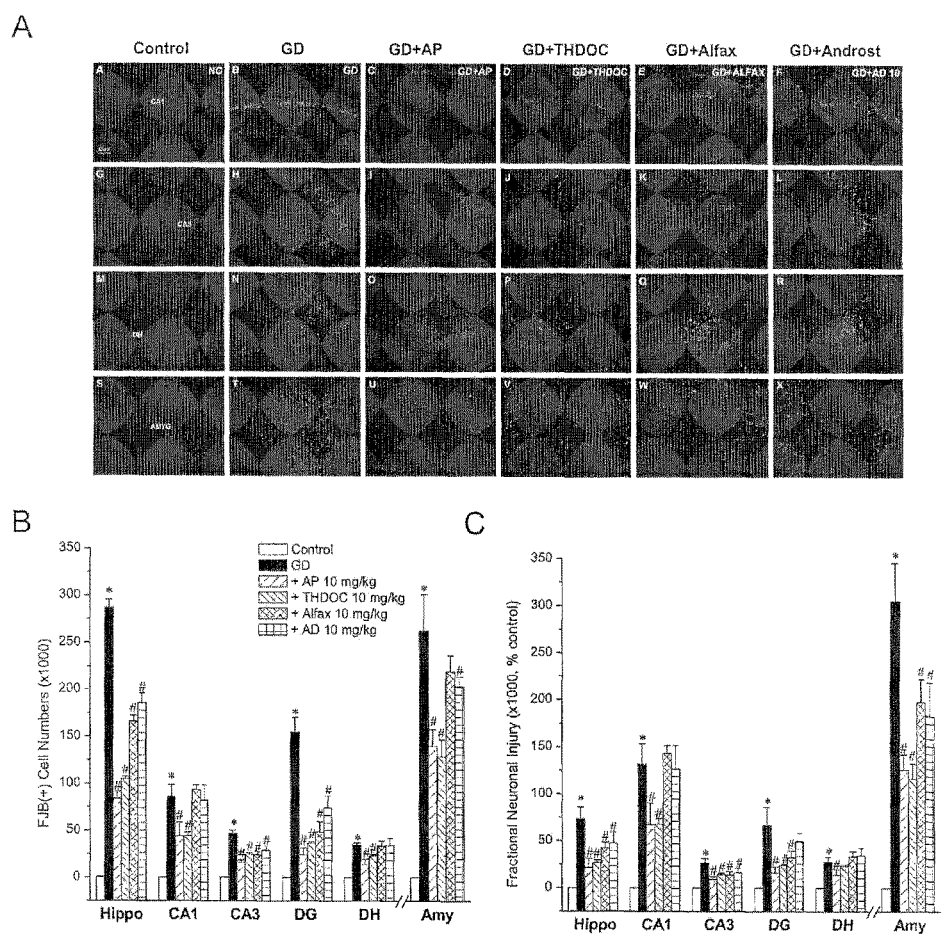

FIG. 8A-C presents exemplary data showing efficacy of delayed treatment with neurosteroids allopregnanolone (10 mg/kg, IM), THDOC (10 mg/kg, IM), alfaxolone (10 mg/kg, IM) and androstanediol (100 mg/kg; IM) against the nerve agent soman-induced OP intoxication related acute neuronal damage within the brain hippocampus subfields (CA1, CA3 & dentate hilus) and amygdala. (A) Time-course profile of neuroprotectant activity ganaxolone treatment in the soman model in rats. Representative confocal images show FJB-positive neurons within the hippocampus subfields and amygdala. (B) Absolute quantification of FJB-positive cell counts in the hippocampus subfields as determined unbiased neurostereology technique. Data represent mean±SEM (N=4-6 rats per group). (C) Protective effect of ganaxolone on acute neuronal injury as determined by percent of FJB-positive cell counts in the hippocampus subfields and amygdala as compared to control group. Data represent mean±SEM (N=4-6 rats per group). *P<0.01 as compared to control group as determined by one-way ANOVA with post hoc student's t-test.

Figure 9:
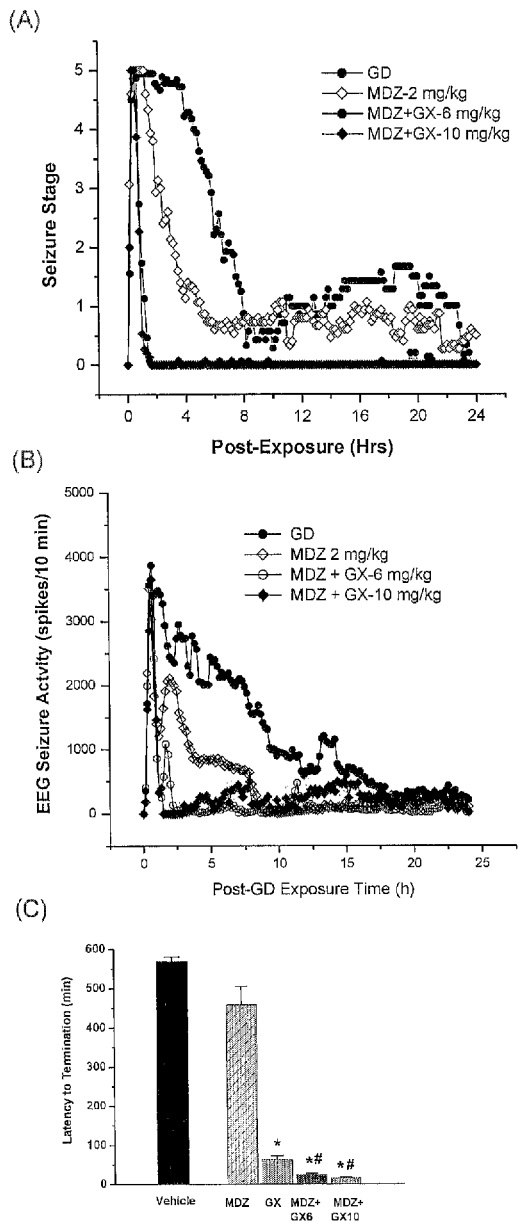

FIG. 9A-C presents exemplary data showing the comparative efficacy of delayed treatment (40-min) with midazolam (2 mg/kg, IM) and ganaxolone (6 & 10 mg/kg, IM) against the nerve agent soman-induced OP intoxication, seizures and status epilepticus. (A) Time-course behavioral profile of protective activity of midazolam, ganaxolone and their combination against OP intoxication caused by soman exposure in rats. (B) Time-course EEG profile of protective activity of midazolam, ganaxolone and their combination against OP intoxication caused by soman exposure in rats. (C) Latency for termination of soman-induced seizures or status epilepticus by ganaxolone treatment in rats. Midazolam, ganaxolone and their combination against was given at 40 min after soman exposure and behavioral stages and EEG seizure activity were monitored continuously for 24 h. Data presented as mean or mean±SEM (n=7 to 12 rats in each group). *P<0.01 as compared to control group as determined by one-way ANOVA with post hoc student's t-test.

Figure 10:
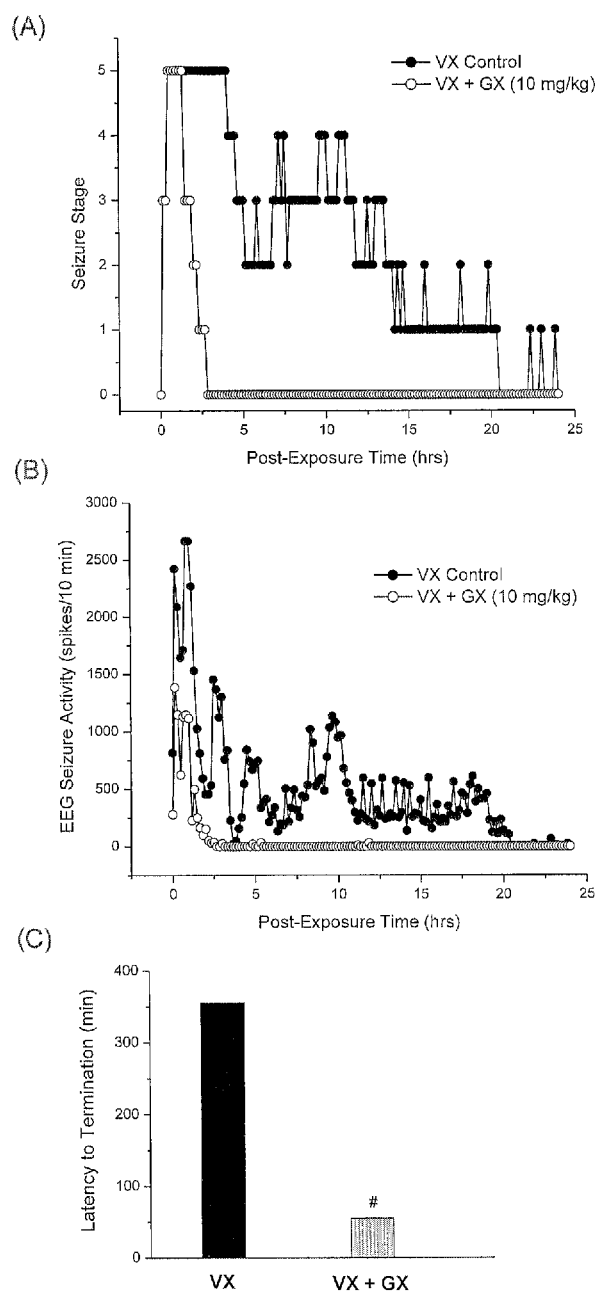

FIG. 10A-C presents exemplary data showing efficacy of delayed treatment with ganaxolone (10 mg/kg, IM) against the nerve agent VX-induced OP intoxication, seizures and status epilepticus. (A) Time-course behavioral profile of protective activity of ganaxolone against OP intoxication caused by VX exposure in rats. (B) Time-course EEG profile of protective activity of ganaxolone against OP intoxication caused by VX exposure in rats. (C) Latency for termination of VX-induced seizures or status epilepticus by ganaxolone treatment in rats. Ganaxolone was given at 40 min after VX exposure and behavioral stages and EEG seizure activity were monitored continuously for 24 h. Data presented as mean from n=6 rats in each group. #P<0.01 as compared to VX control group.

Figure 11:
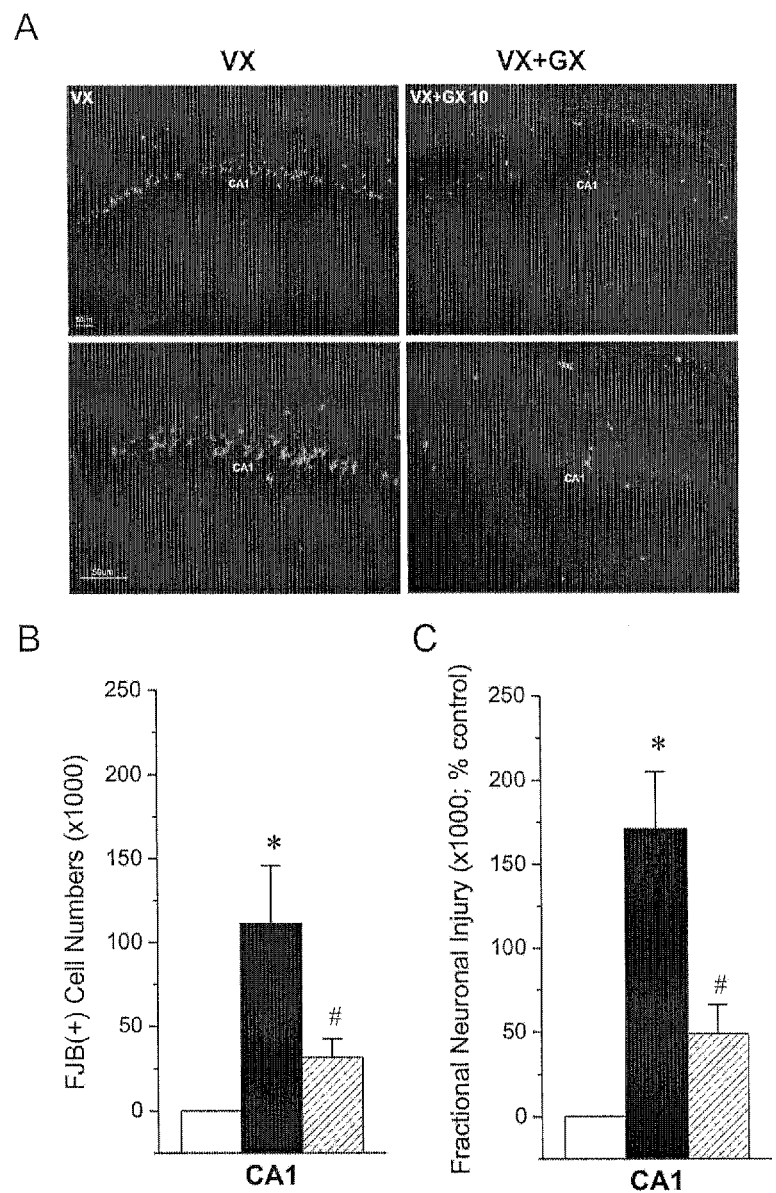
Figure 12:
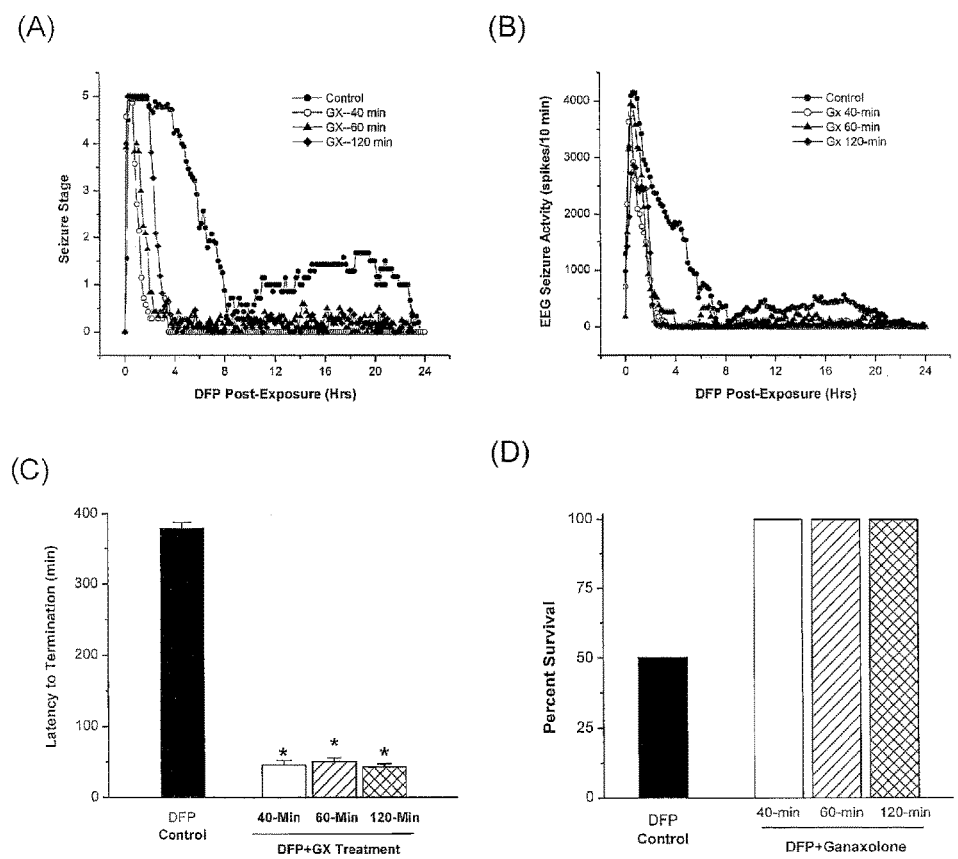

FIG. 11A-C presents exemplary data showing efficacy of delayed treatment with ganaxolone (10 mg/kg, IM) against the nerve agent VX-induced acute neuronal damage within the brain hippocampus CA1 region. (A) Representative florescent images show FJB-positive neurons in the hippocampus CA1 region in VX control and ganaxolone-treated animal (B) Absolute quantification of FJB-positive cell counts in the CA1 subfield as determined unbiased neurostereology technique. Data represent mean±SEM (N=4-5 rats per group). (C) Protective effect of ganaxolone on acute neuronal injury as determined by percent of FJB-positive cell counts in the CA1 subfield as compared to control group. Ganaxolone was given at 40 min after VX exposure and brain perfusions were done 24 h post-VX. Data represent mean±SEM (N=4-5 rats per group). *P<0.01 as compared to control group as determined by one-way ANOVA with post hoc student's t-test.

FIG. 12A-D presents exemplary data showing efficacy of delayed treatment with ganaxolone (6 mg/kg, im) against the pesticide agent DFP-induced OF intoxication, seizures and status epilepticus. (A) Time-course behavioral profile of protective activity of ganaxolone against OP intoxication caused by DFP exposure in rats. (B) Time-course EEG profile of protective activity of ganaxolone against OP intoxication caused by DFP exposure in rats. (C) Latency for termination of DFP-induced seizures or status epilepticus by ganaxolone treatment in rats. (D) Mortality rate in control (untreated) and ganaxolone treatment groups in the DFP model. Ganaxolone was given at 40, 60 or 120 min after DFP exposure and behavioral stages and EEG seizure activity were monitored continuously for 24 h. Data presented as mean or mean±SEM (n=8 to 12 rats in each group). *P<0.01 as compared to control group as determined, by one-way ANOVA with post hoc student's t-test.

Figure 13:
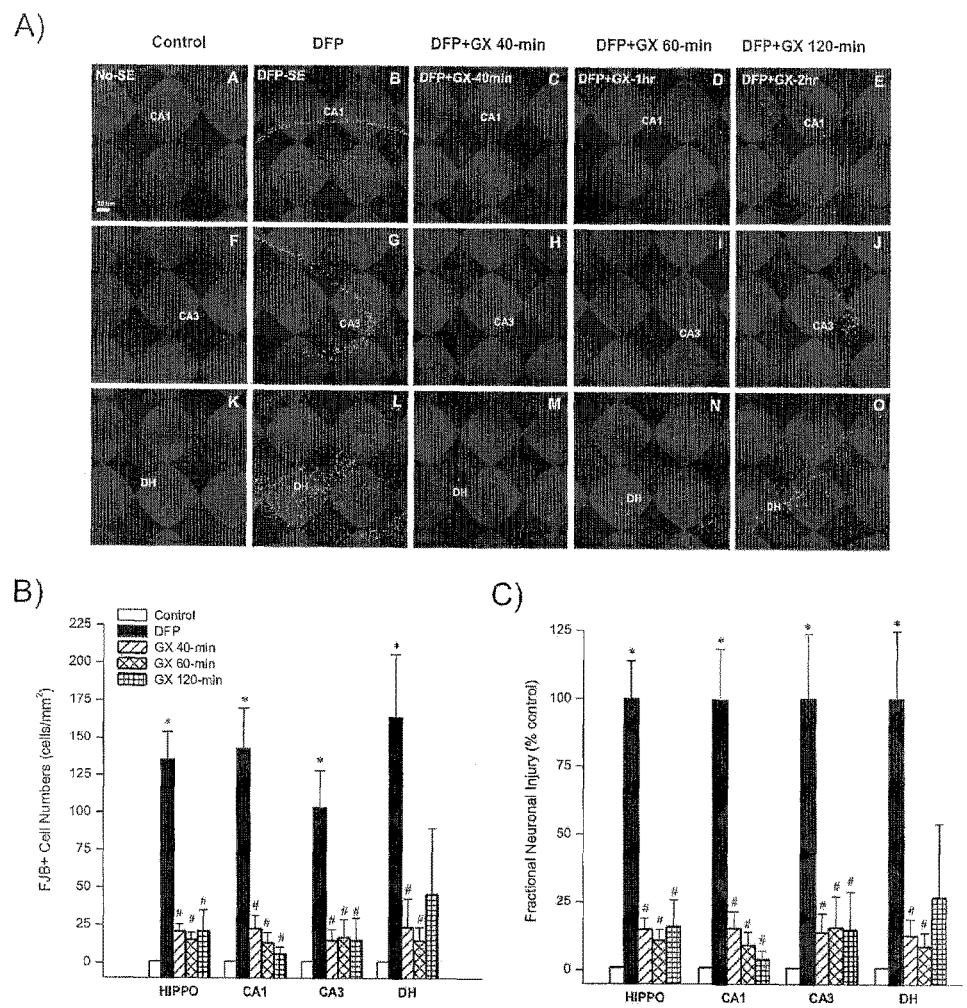
Figure 14:
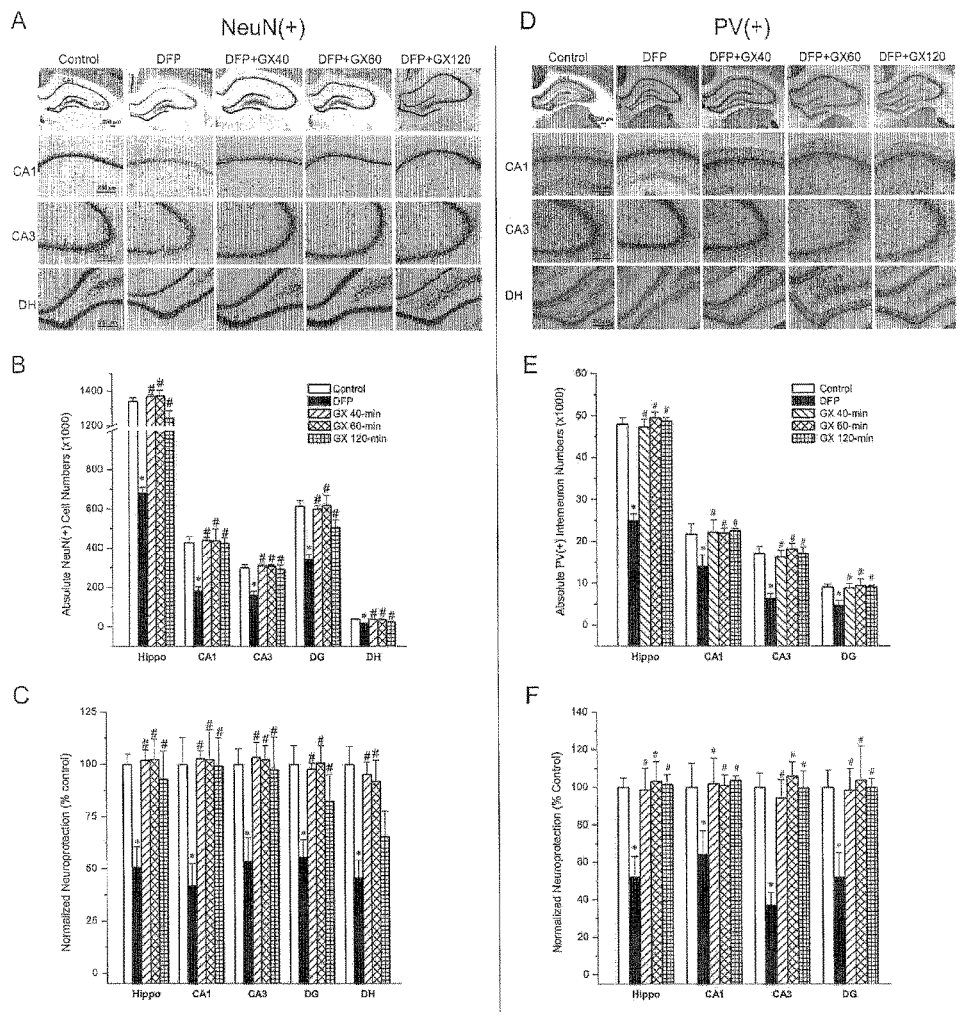

FIG. 13A-C presents exemplary data showing efficacy of delayed treatment with ganaxolone against the pesticide agent DFP-induced OP intoxication related acute neuronal damage within the hippocampus subfields CA1, CA3 and dentate hilus. (A) Time-course profile of neuroprotectant activity ganaxolone treatment (6 mg/kg, im) in the DFP model in rats. Representative confocal images show FJB-positive neurons within the hippocampus subfields as (B) Absolute quantification of FJB-positive cell counts in the hippocampus subfields as determined unbiased neurostereology technique. Data represent mean±SEM (N=4-6 rats per group). (C) Protective effect of ganaxolone on acute neuronal injury as determined by percent of FJB-positive cell counts in the hippocampus subfields as compared to control group. Data represent mean±SEM (N=4-6 rats per group). *P<0.01 as compared to control group as determined by one-way ANOVA with post hoc student's t-test.

FIG. 14A-F presents exemplary data showing the neuroprotectant activity of delayed ganaxolone treatment (6 mg/kg, im) in DFP-induced neuronal cell death and neurodegeneration in rats. (A) Bright-field images show NeuN-positive principal neurons within the hippocampus subfields CA1, CA3 and dentate hilus. (B) Absolute quantification of NeuN-positive principal neurons in the hippocampus subfields by unbiased neurostereology. (C) The extend of neuroprotection of NeuN(+) principal neurons by ganaxolone treatment at 40, 60 and 120 min after DFP exposure as compared to untreated DFP control group. (D) Bright-field images show parvalbumin (PV)-positive GABAergic inhibitory interneurons within the hippocampus subfields CA1, CA3 and dentate hilus. (E) Absolute quantification of PV-positive interneurons neurons in the hippocampus subfields by unbiased neurostereology. (F) The extent of neuroprotection of PV(+) interneurons by ganaxolone treatment at 40, 60 and 120 min after DFO exposure as compared to untreated soman control group. Data represent mean±SEM (N=4-7 rats per group).

Figure 15:
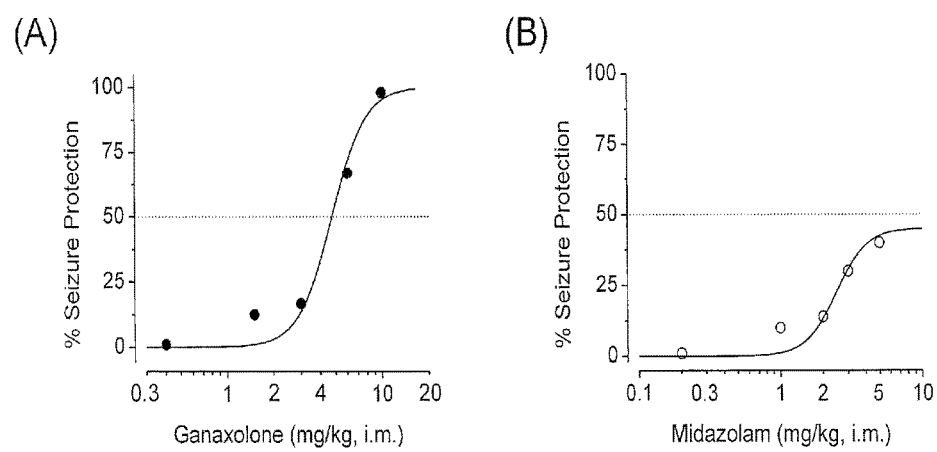

FIG. 15A-B presents exemplary data showing the comparative protective efficacy of delayed ganaxolone and the benzodiazepine midazolam treatment against the DFP-induced OP intoxication, seizures and status epilepticus. (A) The protective $ED_{50}$ value of ganaxolone was calculated from the dose-response data from ganaxolone treatment (1.5-10 mg/kg, im) administered 40 min after DFP exposure in rats. (B) The protective $ED_{50}$ value of midazolam was estimated from the dose-response data from midazolam treatment (0.2-5 mg/kg, im) administered 40 min after DFP exposure in rats. Each data point represents the mean protection from a group of 6 to 12 rats at each dose level.

Figure 16:
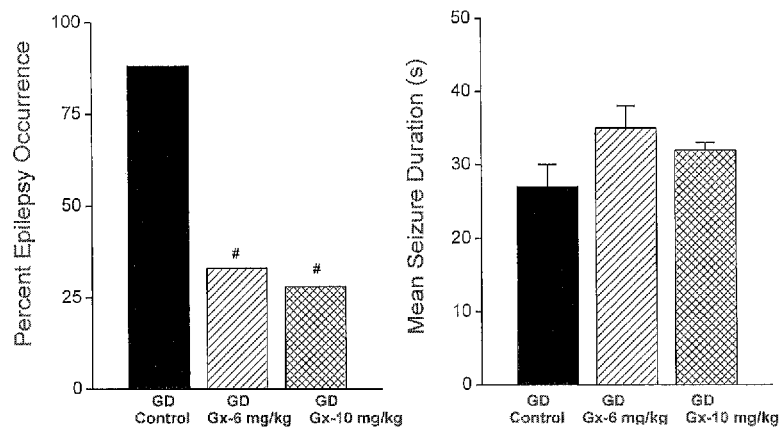
Figure 16:
Figure 16:
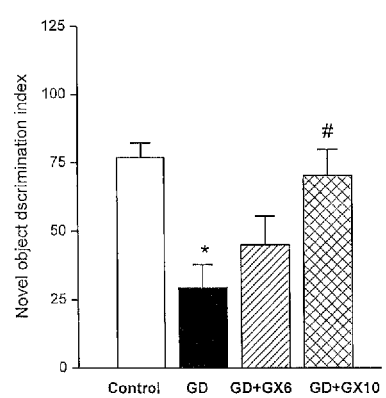

FIG. 16A-C presents exemplary data showing the attenuating activity of ganaxolone treatment (6 & 10 mg/kg, im) against soman-induced long-term cognitive neurobehavioral and epileptogenic dysfunction in rats. (A) Reduced epileptogenic rate in ganaxolone-treated rats 3 months alter OP intoxication as assessed by video-EEG monitoring from 1 to 3 months post-soman (GD) exposure. (B) Representative EEG traces of spontaneous seizures in soman and ganaxolone-treated rat. (C) Reduced non-spatial memory deficits in ganaxolone-treated rats 3 months after OP intoxication as assessed in the novel object recognition test (NOR). Data represent mean±SEM (N=6-8 rats per group). *P<0.01 as compared to GD control group.

Figure 17:
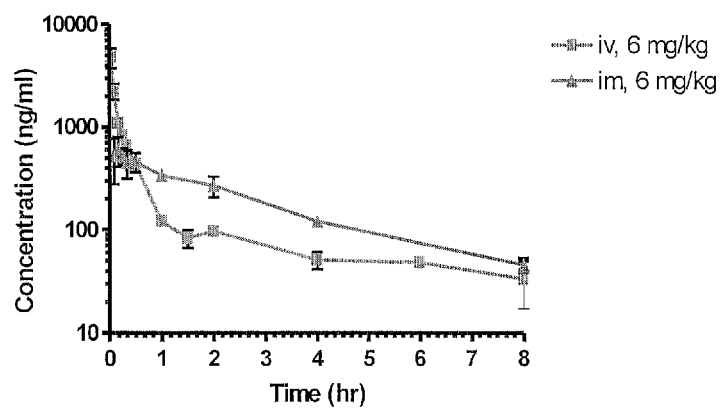
Figure 17:
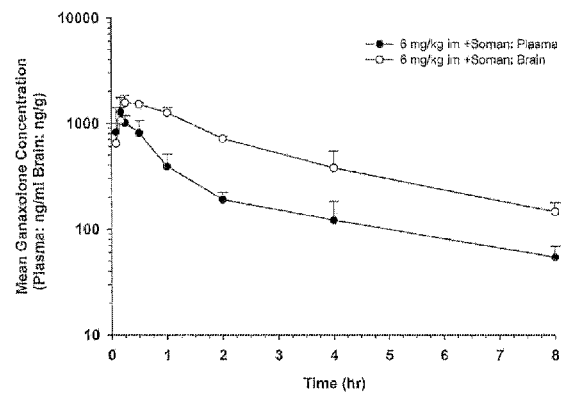

FIG. 17A-B presents exemplary data showing the pharmacokinetics of ganaxolone in control and soman exposed rats. (A) Pharmacokinetics study of ganaxolone following a single dose administration to naïve male Sprague-Dawley rats. Time-course of mean ganaxolone plasma concentrations after an intravenous (iv) or Intramuscular (im) dose of 6 mg/kg ganaxolone in rats. (B) Plasma and brain pharmacokinetics of ganaxolone following intramuscular injection in soman-exposed rats. Time-course of mean ganaxolone concentrations in plasma and brain after an im dose of 6 mg/kg ganaxolone in soman exposed male rats. Each data point represents the mean±SD from n=5 rats plotted against nominal times.

DETAILED DESCRIPTION OF THE INVENTION

The present invention is related to the field of organophosphate intoxication. Compositions and methods are disclosed that provide an effective post-exposure treatment of organophosphate intoxication. Such treatment not only reverses organophosphate intoxication more effectively than benzodiazepines but prevents subsequent neuronal injury and long-term neuropsychiatric deficits. For example, neurosteroid compounds either alone, or in combination with conventional organophosphate antidotes including, but not limited to, atropine and/or pralidoxime are provided.

Figure 1:
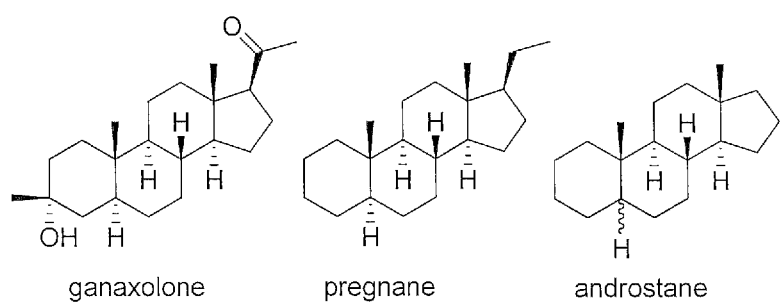
FIG. 1 presents chemical structures of three representative neurosteroids useful in the present invention; ganaoxolone, pregnane and androstane.

In one embodiment, the present invention contemplates compositions and methods for treating or reversing organophosphate intoxication and manifestations in a mammal resulting from exposure to nerve agents, organophosphates (OP) and incapacitating agents of the central nervous system. For example, neurosteroidal compounds of this invention include, but are not limited to, those having a general structural formula of pregnane, androstane, 19-norandrostanes, and/or norpregnane. Such nonsteroidal compounds may also comprise further moieties as defined herein as having seizure modulating and/or neuroprotection properties including, but not limited to, ganaxolone, pregnenolone, and androstanediol and their analogs, salts and prodrugs. See, FIG. 1.

In one embodiment, the present invention contemplates a method of treating an animal subject, including humans, exposed to organophosphates comprising administering a therapeutically effective amount of a neurosteroidal compound, given alone and/or in combination with standard nerve agent antidote regimens (e.g., for example, atropine, pralidoxime) earlier or later than forty (40) minutes after exposure. In one embodiment, compositions contemplated by the present invention preferably comprise effective amounts of at least one neurosteroidal compound and a pharmaceutical carrier in an acceptable dosage formulation for administration by parenteral or other routes of administration up to several hours after exposure of an individual to nerve agents. In one embodiment, the said pharmaceutical composition has an improved effectiveness in treating organophosphate intoxication than benzodiazepine agents selected from the group consists of midazolam and diazepam.

In one embodiment, the present invention contemplates neurosteroids that provide an effective treatment for organophosphate intoxication such as nerve agent or pesticide intoxication including, but not limited to, cluster symptoms of organophosphate chemical intoxication, delayed intoxication, benzodiazepine-refractory intoxication, manifested as neuronal injury, neuronal loss, neurodegeneration, axonal degeneration, blood-brain barrier dysfunction, neuroinflammation, hyperactivity, excitability, hyperexcitability, synchronous activity, epileptiform discharges, mossy fiber sprouting, and central nervous system (CNS) signs and symptoms of intoxication or cholinergic hyperactivation caused by organophosphate exposure, referred as cholinergic crisis and non-cholinergic crisis. The disclosed neurosteroid method of treatment will help limiting or preventing acute brain damage at the early stage of OP poisoning and attenuate the subsequent neurological dysfunction, and thus reducing the long-term disability caused by exposure to organophosphates. In one embodiment, the said pharmaceutical composition has an improved effectiveness in treating organophosphate intoxication than benzodiazepine agents selected from the group consists of midazolam and diazepam.

I. Conventional Organophosphate Intoxication Treatments

Current antidotes for organophosphate intoxication consist of a pretreatment with carbamates to protect AChE from inhibition by organophosphate compounds and post-exposure treatments with anti-cholinergics and pyridinium oximes. Anti-cholinergic drugs work to counteract the effects of excess acetylcholine and reactivate AChE. Atropine can be used as an antidote in conjunction with pralidoxime or other pyridinium oximes (such as trimedoxime or obidoxime). Charged quaternary pyridinium oximes such as pralidoxime (2-PAM) are currently used as antidotes for OP intoxication. Such drugs reactivate AChE which has undergone covalent modification by OP chemical nerve agents. Jakanović et al., "Pyridinium oximes as cholinesterase reactivators. Structure-activity relationship and efficacy in the treatment of poisoning with organophosphorus compounds" Curr. Med. Chem. 16 (17): 2177-2188 (2009); and Balali-Mood et al., "Treatment of organophosphate poisoning. Experience of nerve agents and acute pesticide poisoning on the effects oximes" J Physiology 92: 375-378 (1998). However, the use of "-oximes" has been found to be of no benefit, or possibly harmful, in at least two meta-analyses. Rahimi et al., "Increased morbidity and mortality in acute human organophosphate-poisoned patients treated by oximes: a meta-analysis of clinical trials" Hum Exp Toxicol 25 (3): 157-162 (2006); and Peter et al., "Oxime therapy and outcomes in human organophosphate poisoning: an evaluation using meta-analytic techniques" Crit. Care Med. 34 (2):502-510 (2006). The major limitation of these drugs is poor CNS bioavailability owing to the permanent positive charge and lack of suitable active transporters at the blood brain barrier. Therefore, currently fielded oximes (e.g. 2-PAM, obidoxime, and HI-6) cannot directly reactivate nerve agent-inhibited AChE in the brain, which a critical target organ for nerve agents and OP pesticides. As a result, there is little neurological protection from 2-PAM treatment.

The most commonly used post-exposure treatment, atropine, is a muscarinic antagonist and blocks peripheral muscarinic acetylcholinesterase receptors. Walker C (2001). In: Organic Pollutants: An Ecotoxicological Perspective. Eds: Taylor & Francis, pp. 186-193. ISBN 0-7484-0962-9. Atropine antidotes are effective at preventing lethality from organophosphate intoxication, but current treatment lack the ability to prevent post-exposure incapacitation, performance deficits, or permanent brain damage. Doctor et al., "Bioscavengers for the protection of humans against organophosphate toxicity" Chemico-Biological Interactions 157/158: 167-171 (2005). Unlike atropine, pralidoxime (alone) has not been observed to have substantial clinical efficacy in treatment of organophosphate intoxication. Banerjee et al., "Efficacy of pralidoxime in organophosphorus poisoning: Revisiting the controversy in Indian setting" J Postgrad Med 60:27-30 (2014) While atropine is highly effective in antagonizing ACh at most peripheral muscarinic receptors and partly at central muscarinic receptors, atropine is ineffective at nicotinic receptors and intoxication mediated by such receptors in the brain and peripheral system. Moreover, atropine cannot effectively mitigate the central muscarinic or nicotinic effects of OP intoxication due to its limited ability to enter into the brain. Therefore, OP intoxication immediately proceeds with generalized seizures and brain damage despite atropine therapy. New and effective neuroprotective agents are needed to reduce such neurologic sequelae induced by OP intoxication.

Alternatively, enzyme bioscavengers are being developed as a pretreatment to sequester highly toxic organophosphates before they can reach their physiological targets and prevent the toxic effects from occurring. Significant advances with cholinesterases (ChEs), specifically human serum BChE (HuBChE) have been made. HuBChe can offer a broad range of protection for nerve agents including soman, sarin, tabun, and VX. HuBChE also possess a very long retention time in the human circulation system and because it is from a human source it will not produce any antagonixtic immunological responses. HuBChE is currently being assessed for inclusion into the protective regimen against organophosphate nerve agent intoxication. Currently, there is also potential for PON1 to be used to treat sarin exposure, but recombinant PON1 variants would need to first be generated to increase its catalytic efficiency. Doctor et al., "bioscavengers for the protection of humans against organophosphate toxicity" Chemico-Biological Interactions 157/158: 167-171 (2005).

Anti-arrhythmic agents are also under consideration to treat organophosphate intoxication-induced hyperkalemia. While the cellular processes leading to cardiac toxicity are not well understood, the potassium current channels are believed to be involved. Zoltani et al., "Organophosphate Caused Cardia Toxicity: Action Potential Dynamics in Atrial Tissue" Army Research Laboratory 1-15 (2002).

Currently, there are few effective medications for delayed treatment (e.g., 40 min or later) of signs and symptoms due to organophosphate (OP) intoxication. Medical treatment or organophosphate intoxication earlier than 40 min is not practical in most instances of mass chemical exposure due to time needed for first responders to respond to such unexpected event. Therefore, the presently disclosed neurosteroids offer advantages because they can be an effective treatment even after few hours delay after OP exposure. In particular, it has not been reported that a neurosteroid, when administered alone, is an effective treatment for organophosphate intoxication.

It is known that organophosphate intoxication is both dose and time-dependent, wherein a response to treatment of toxic signs is depesident upon both the degree of exposure and the sensitivity threshold of the individual. The data presented herein suggests that neurosteroids, provide an effective treatment when administered between approximately forty (40) minutes and two (2) hours after exposure to an organophosphate.

Presently, most efforts to treat organophosphate symptoms have focused upon the appearance of seizures (i.e., for example, only one symptom of many). Status epilepticus (SE) is a life-threatening emergency characterized by a prolonged continuous state of convulsions. SB is defined as continuous seizure activity or multiple seizures without regaining consciousness for more than 30 min. SE is a medical emergency in humans that if untreated, can lead to brain damage and death. There are two types of SE, generalized convulsive SE and nonconvulsive SE. Untreated SE can result in death due to an inability of the brain to control and terminate the seizures. The pathophysiology of SE is complex but excess excitatory (glutamate) neurotransmission and loss of normal inhibitory (GABA) neurotransmission are thought to be the most likely mechanisms.

SE that is non-responsive to benzodiazepines or other anticonvulsants is known as "refractory SE". In experimental models, a variety of chemicals can cause SE including pilocarpine, kainic acid, flurothyl cobalt-homocysteine thiolactone, 4-aminopyridine, and OP pesticides and nerve agents. Biomarker/diagnosis of SE include seizure signs and EEG spike activity. Patient medical history or information of injury, accident or brain conditions are helpful.

Benzodiazepines that are positive allosteric modulators of GABA-A receptors have long been the first line of treatment for the control of seizures and SB induced by OP intoxication and other conditions that trigger acute seizures. The benzodiazepine diazepam is currently the only FDA-approved injectable anticonvulsant for the cessation of seizures caused by nerve agents and OP pesticides. However, there are many serious concerns with the use of diazepam for controlling nerve agent seizures: (i) The efficacy of diazepam decreases as the interval between the OP intoxication or initiation of seizures and the administration of diazepam increases. Diazepam must be administered within 10 to 30 minutes of OP intoxication or nerve gas exposures, after which there is no protection against seizures and progressive neurological damage occurs. McDonough et al. "Time-dependent reduction in the anticonvulsant clinical effectiveness of diazepam against soman-induced seizures in guinea pigs" *Drug Chem Toxicol* 33 (3):279-83 (2010). This timeline is often not practical in many incidents including emergencies and mass casualties. The development of resistance to diazepam is a concern because by the time the subject receives medical assistance after chemical agents, the seizures may have already become resistant to benzodiazepines. (ii) Seizures often recur after termination of the initial SE by benzodiazepines. This is particularly problematic considering that the duration and intensity of seizures clearly correlate with the severity of the resulting neuropathology. Mayer et al. "Refractory status epilepticus: frequency, risk factors, and impact on outcome" *Arch Neurol* 59:205-210 (2002); Prager et al. "The recovery of acetylcholinesterase activity and the progression of neuropathological and pathophysiological alterations in the rat basolateral amygdala after soman-induced status epilepticus: Relation to anxiety-like behavior. *Neuropharmacology* 81:64-74 (2014). Seizures induced by OP intoxication can become self-sustaining and develop time-dependent refractory SE—a serious condition with significant brain injury and mortality, Wasterlain et al. "Molecular basis of self-sustaining seizures and pharmacoresistance during status epilapticus: The receptor trafficking hypothesis revisited" *Epilepsia* 50 (S12):16-38 (2009). Benzodiazepines including diazepam and midazolam are not sufficiently protective against refractory SE and neurodegeneration that occurs at later times after nerve agent exposure. Apland et al. "The limitations of diazepam as a treatment for nerve agent-induced seizures and neuropathology in rats: comparison with UBP302" *J Pharmacol Exp Ther.* 351:359-72 (2014). (iii) Benzodiazepines are among the anticonvulsants with variable pharmacokinetics and serious side effects. Kellinghaus et al. "Treatment of status epilepticus in a large community hospital" *Epilepsy Behav* 23:235-240 (2012). The diazepam intramuscular autoinjectors are distributed as part of the military kit in case of a chemical attacks or accidents. Diazepam is erratically absorbed via intramuscular autoinjectors. Moreover, repeated high doses of diazepam are needed to control recurrent seizures, resulting in sedation, respiratory depression and tolerance. Thus, the practical utility of benzodiazepines (diazepam and midazolam) for nerve gas exposure is limited and uncertain because they must be given within minutes of an attack to be effective. They are not effective for late-stage seizures, especially SE that cause profound brain damage. Reddy et al. "Midazolam as an anticonvulsant antidote for organophosphate intoxication—A pharmacotherapeutic appraisal" *Epilepsia* 56:813-821 (2015).

Combinations of a benzodiazepine and neurosteroids have been reported to prevent or terminate seizures. Such neurosteroids included allopregnanolone, allotetrahydrodeoxycorticosterone, ganaxolone, alphaxolone, alphadolone, hydroxydione, minaxolone, and Althesin. This combination therapy is described in both the context of both natural seizures and for those that are a result of exposure to a nerve agent or a pesticide, including organophosphorus nerve agents, but not for the condition of organophosphate-induced intoxication. Such nerve agents that can cause seizures to include, e.g., organophosphorus nerve agents, e.g., tabun, sarin, soman, cyclosarin (GF), N,N-diethyl-2-(methyl-(2-methylpropoxy) phosphoryl)sulfanylethanamin (VR) and/or VX and illustrative pesticides that can cause seizures include, e.g., organophosphate pesticides. The administration of only neurosteroids for the purpose of treating nerve agent-induced intoxication is not suggested. Rogawski et al., "Mitigation of Epileptic Seizures by Combination Therapy Using Benzodiazepines and Neurosteroids" U.S. Patent Application Publication No. US 2014/0050789; and Rogawski et al., "Intrapulmonary Benzodiazepine for the Treatment and Prevention of Seizures" U.S. Patent Application Publication No. US 2013/0309306. Epilepsy has also been treated with the administration of a neuroactive steroid (e.g., allopregnanolone), either alone, or in combination with a benzodiazepine, Reddy et al., "Methods of Treating Epilepsy or Status Epilepticus," U.S. Patent Application Publication No. US 2014/0057885.

The use of benzodiazepine (e.g., midazolam) treatment of organophosphate poisoning induced status epilepticus was effective in preventing paraoxon-induced chronic epilepsy if administered 1 min after seizures onset, but not 30 min thereafter. Shrot et al., "Prevention of Organophosphate-induced Chronic Epilepsy by Early Benzodiazepine Treatment" *Toxicology* 323:19-25 (2014). It was suggested that organophosphate antidote kits have a combination dose of a benzodiazepine and conventionally used compounds, such as atropine and/or an oxime.

Other therapeutic drug combinations have also been tried to treat organophosphate poisoning. For example, combinations of atropine, an oxime, and a benzodiazepine. Rosenbaum et al., "Non-Muscarinic Therapeutic Targets for Acute Organophosphorus Poisoning" *J. Med. Toxicol.* 6 (4):408-412 (2010).

Summary of limitations of current medical countermeasures for OP intoxication: Presently there are few effective antidotes for OP intoxication, especially for rapid and effective termination of the neurotoxic manifestations, seizures and brain damage. Pyridostigmine bromide is FDA-approved for use as a pretreatment, but it has limited usefulness in post-exposure emergencies. Current treatment for nerve agent and OP intoxication includes a specialized drag combination containing; (i) Atropine sulfate—a muscarinic receptor antagonist; (ii) 2-PAM (pralidoxime chloride)—a drug to regenerate acetylcholinesterase activity; and (iii) Diazepam—a benzodiazepine anticonvulsant. Bajgar "Organophosphates/nerve agent poisoning: mechanism of action, diagnosis, prophylaxis; and treatment" *Adv Clin Chem* 38:151-216 (2004); Eddleston et al. "Management of acute organophosphorus pesticide poisoning" *Lancet* 371 (9612):597-607 (2008). This regimen is distributed as CHEMPACKs with autoinjectors for use in case of a chemical attack or accident. However, benzodiazepines have significant limitations. These agents must be administered within 10 to 30 minutes, after which there is no protection against seizures and progressive neurological damage occurs. This timeline is often not practical in many incidents including emergencies and mass casualties. Diazepam is erratically absorbed via intramuscular autoinjectors. Moreover, repeated high doses of diazepam are needed to control recurrent seizures, resulting in sedation, respiratory depression and tolerance. Seizures induced by OP intoxication can become self-sustaining and develop time-dependent refractory SE with over 25% mortality. Benzodiazepines including diazepam and midazolam are not sufficiently protective against refractory SE and neurodegeneration that occurs at later times after nerve agent exposure. Therefore, there is an urgent need for new non-benzodiazepines for rapid and effective control of OP intoxication and its manifestations including seizures and neurodegeneration.

II. Organophosphate Intoxication

Organophosphate (OP) pesticides and nerve agents are chemical threat agents. Nerve agents are chemical warfare agents that have long attracted the attention of terrorists for attacking a civilian population. Classic nerve agents ("gases" sarin, soman, tabun, cyclosarin, and VX) directly target the nervous system and irreversibly impair neural signaling within minutes of exposure. Soman is one of the most lethal nerve gases, with a rat $LD_{50}$~110 µg/kg (5-8). OP pesticides such as diisopropyl-fluorophosphate or DFP, parathion, and paraoxon are considered credible threat agents because they are readily obtainable and are highly neurotoxic when exposed by a deliberate terrorist aback, or by accident or natural disaster (9-13). DFP is one of the most potent neurotoxic OP pesticides, with $LD_{50}$~1.3 mg/kg in rats (12-14). DFP is very similar in structure to the nerve agents soman and sarin. DFP is widely accepted as a surrogate agent for nerve agents. Such pesticides could be used in an act of terrorism. Military nerve agents and civilian OP pesticides are extremely lethal and produce neurotoxicity via common mechanisms. They cause devastating damage to the brain primarily due to their irreversible inhibition of acetylcholinesterase, leading to an excessive accumulation of acetylcholine (ACh), a powerful excitatory neurotransmitter in the brain. Acute exposure to nerve gases or OP poisoning results in cholinergic hyperactivation and causes a set of predictable toxic signs: hypersecretion, fasciculations, tremors, convulsions, respiratory distress and death. CNS manifestations following nerve agent exposure include convulsive seizures and status epilepticus (SE), which can last 30 min or longer with profound brain damage, resulting in death, or long-term neuronal damage. The effects of nerve intoxication are very long lasting and survivors suffer chronic brain damage including the risk of neurological and cognitive deficits.

Jett et al. "The CounterACT Research Network: basic mechanisms and practical applications" *Proc Am Thorac Soc* 7:254-256 (2010); Bajgar "Complex view on poisoning with nerve agents and organophosphates" *Acta Medica (Hradec Kralove)* 48: 3-21 (2005).

Exposure to an organophosphate (OP) pesticides or nerve agents produces a characteristic set of signs and symptoms due to OP intoxication. Two distinct toxic syndromes are evident: cholinergic crisis (cholinergic effects) and non-cholinergic neurotoxicity (excitotoxicity).

Acute organophosphate intoxication manifests as a "cholinergic crisis" characterized by a set of progressive toxic signs and manifestations including, but not limited to, hypersecretions, fasciculations, tremor, respiratory distress, bradycardia, hypotension, convulsions/seizures, coma and/or death. See, Table 1.

TABLE 1

Cholinergic Crisis Symptomology

| Muscarinic symptomatology | Nicotinic symptomatology | Central nervous symptoms |
| --- | --- | --- |
| Myosis | Muscular fasciculation | anxiety, agitation, tremor; |
| Bradicardia | Muscular weakness | consciousness alteration; |
| Hypotension | Muscular paralysis | hallucinations; |
| Bronchorrhoea | Respiratory insufficiency | seizures; |
| Salivation | (ventilatory component) | respiratory centre inhibition - |
| Emesis | Pallor | respiratory insufficiency |
| Diarrhea, abdominal pain | Perspiration | (synergistic with |
| Urinary frequency | Mydriasys* | skeletal muscle paralysis) |
| Cardiac rhythm disturbance | Tachycardia* | hypothermia |
|  | Hypertension* | intermediate syndrome - |
|  | *(Transient symptoms usually masked by muscarinic symptomatology) | type II paralysis - appears few days later |

Organophosphate intoxication may be caused by chemical agents that can irreversibly inhibit AChE enzyme activity such as by: i) nerve agents including, but not limited to, tabun, sarin, soman, cyclosarin, VX, VR and other nerve gases; and ii) pesticides including, but not limited to, parathion, paraoxon, diisopropyl-fluorophosphate, chlorpyrifos, monocrotophos and many other pesticides and insecticides with organophosphate structure.

These toxic effects of nerve agents and organophosphate pesticides are due to hyperactivity of the cholinergic system as a result of inhibition of acetylcholinesterase (AChE), the enzyme that degrades the neurotransmitter acetylcholine (ACh), and the subsequent rapid and sustained increases in the concentrations of ACh at central and peripheral sites. "Cholinergic crisis" results as a consequence of ACh accumulation at postsynaptic sites. Symptoms are different according to the effector organ.

Figure 2:
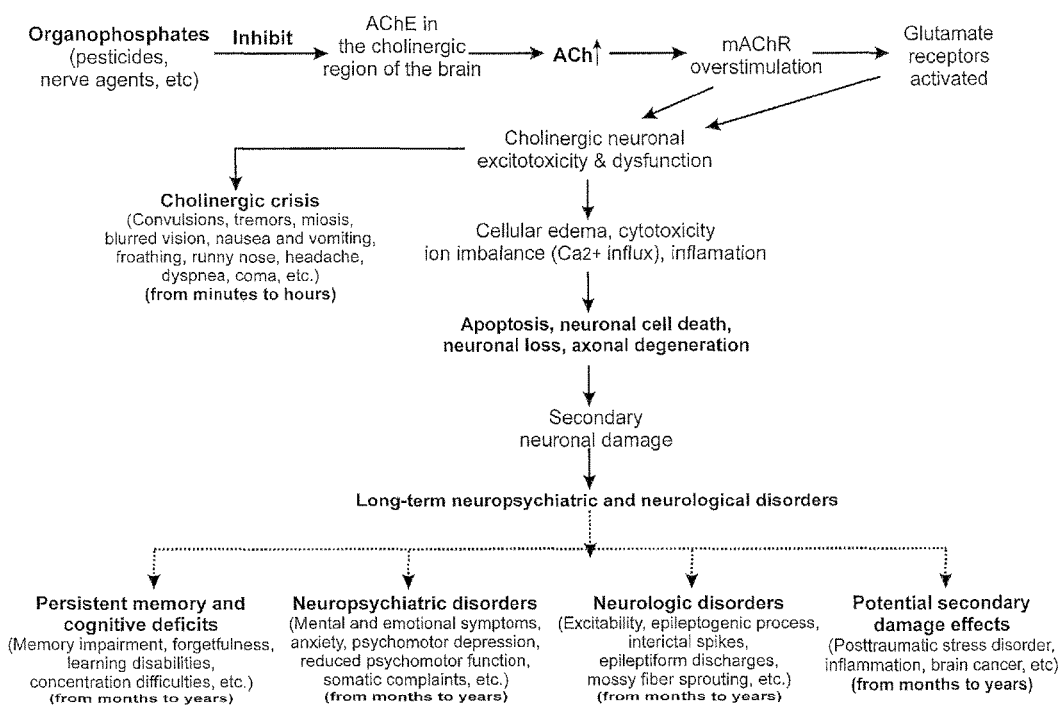
FIG. 2 presents an illustrative schematic of a potential sequence of non-cholinergic pathophysiological symptomology subsequent to organophosphate intoxication.

Organophosphate intoxication also results in "non-cholinergic crisis" producing profound brain damage characterized by neuronal injury, neuronal death, neuroinflammation, hyperactivity, excitability, hyperexcitability, synchronous activity, excitotoxicity, ischemia-hypoxia, atrophy, neuronal dysfunction, neurovascular damage, and deleterious effect on brain structure and function. A similar phenomenon is also observed subsequent to benzodiazepine-refractory intoxication. See, Table 2 and FIG. 2.

TABLE 2

Non-Cholinergic Crisis Symptomology

| | |
|---|---|
| Cerebral edema | Subacute behavioral dysfunction |
| Blood brain barrier dysfunction | Subactute neurological dysfunction |
| Neural Inflammation | Individual neuropsychiatric disorders |
| Non-neuronal inflammation | Clustered neuropsychiatric disorders |
| Neuronal cell apoptosis | |
| Neuronal cell necrosis | |
| Neuronal cell injury | |
| Neuronal cell death | |
| Neuronal cell loss | |
| Axonal degeneration | |
| Axonal sprouting | |
| Neurodegeneration | |

The neuropathological consequences of organophosphate intoxication are dose and time-dependent. Seizures are the typical CNS manifestation of organophosphate intoxication and rapidly progress into status epilepticus, a prolonged electrographic seizures or non-convulsive seizure activity. Organophosphate intoxication may be diagnosed by measuring AChE enzyme activity. For example, initial symptomotology appears at >50% inhibition of AChE, which is closely correlated with OP toxicity and represents a biomarker for organophosphate exposure. Detection of residual metabolites of chemical exposure agent (e.g. sarin metabolites) also provides a definite confirmation of a specific agent.

Many organophosphates are potent nerve agents, functioning by inhibiting the action of acetylcholinesterase (AChE) in nerve cells. They are one of the most common causes of poisoning worldwide, and are frequently intentionally used in suicides in agricultural areas. Organophosphorous pesticides can be absorbed by all routes, including inhalation, ingestion, and dermal absorption. Their inhibitory effect they have on the acetylcholinesterase enzyme leads to a pathologic excess of acetylcholine in the body. Their toxicity is not limited to the acute phase, however, and chronic effects have long been noted. Neurotransmitters such as acetylcholine (which is affected by organophosphate pesticides) are profoundly important in the brain's development, and many organophosphates have neurotoxic effects on developing organisms, even from low-levels of exposure. Other organophosphates are not toxic, yet their main metabolites, such as their oxons are. Treatment includes both a pralidoxime binder and an anticholinergic such as atropine.

Repeated or prolonged exposure to organophosphates may result in the same effects as acute exposure including delayed symptoms. Other effects reported in workers repeatedly exposed include impaired memory and concentration, disorientation, severe depressions, irritability, confusion, headache, speech difficulties, delayed reaction times, nightmares, sleepwalking and drowsiness or insomnia. An influenza-like condition with headache, nausea, weakness, loss of appetite, and malaise has also been reported. Even at relatively low levels organophosphates may be hazardous to human health. Pesticides may act on a set of brain chemicals closely related to those involved in ADHD, thus fetuses and voting children, where brain development depends on a strict sequence of biological events, may be most at risk. Jurewicz et al., "Prenatal and Childhood Exposure to Pesticides and Neurobehavioral Development: Review of Epidemiological Studies" *International Journal of Occupational Medicine and Environmental Health* (Versita, Warsaw) 21 (2):121-132 (2008).

Organophosphate poisoning may result from exposure to organophosphates (OPs), which cause the inhibition of acetylcholinesterase (AChE), leading to the accumulation of acetylcholine (ACh) in the body. Organophosphate poisoning most commonly results from exposure to insecticides or nerve agents. OPs are one of the most common causes of poisoning worldwide, and are frequently intentionally used in suicides in agrarian areas. There are around 1 million OP poisonings per year with several hundred thousand resulting in fatalities annually. Pandit et al., "A case of organophosphate poisoning presenting with seizure and unavailable history of parenteral suicide attempt" *J Emerg Trauma Shock* 4 (1):132-134 (2011); and Yurumez et al., "Acute organophosphate poisoning in university hospital emergency room patients" *Intern Med* 46 (13): 965-969 (2007).

Organophosphates inhibit AChE, causing OP intoxication by phosphorylating a serine hydroxyl residue on AChE, which inactivates AChE. AChE plays a role in nerve function, so the irreversible blockage of this enzyme, which causes acetylcholine accumulation, results in muscle overstimulation. This causes disturbances across the cholinergic synapses and can only be reactivated very slowly, if at all. For example, paraoxonase (PON1) is an enzyme involved in OP pesticides and may be involved in determining an organism's sensitivity to OP exposure.

Organophosphate poisoning is believed to be a result of excess acetylcholine (ACh) present at different nerves and receptors in the body because acetylcholinesterase is blocked. For example, accumulation of ACh at motor nerves may cause overstimulation of nicotinic expression at the neuromuscular junction. When this occurs, symptoms such as muscle weakness, fatigue, muscle cramps, fasciculation, and paralysis can be seen. When there is an accumulation of ACh at autonomic ganglia, this may cause an overstimulation of nicotinic receptors m the sympathetic system. Symptoms associated with this are hypertension, and hypoglycemia. Overstimulation of nicotinic acetylcholine receptors in the central nervous system, due to accumulation of ACh, may result in anxiety, headache, convulsions, ataxia, depression of respiration and circulation, tremor, general weakness, and potentially coma. When there is expression of muscarinic overstimulation due to excess acetylcholine at muscarinic acetylcholine receptors symptoms of visual disturbances, tightness in chest, wheezing due to bronchoconstriction, increased bronchial secretions, increased salivation, lacrimation, sweating, peristalsis, and urination can occur. Leibson et al., "Organophosphate and Carbamate Poisoning: Review of the Current Literature and Summary of Clinical and Laboratory Experience in Southern Israel" *J toxicology* 10:767-770 (2008); and Eskenazi et al., "Exposures of Children to Organophosphate Pesticides and Their Potential Adverse Health Effects" *J Environmental Health Perspectives* 107:409-419 (1999). The onset and severity of symptoms, whether acute or chronic, depends upon the specific chemical, the route of exposure, the dose, and the individual's ability to degrade the compound.

Neurotoxic effects have also been linked to organophosphate intoxication causing at least four neurotoxic effects in humans: i) cholinergic crisis (CC); ii) intermediate syndrome (IMS); iii) organophosphate-induced delayed polyneuropathy (OPIDP); and iv) chronic organophosphate-induced neuropsychiatric disorder (COPIND). These syndromes result after acute and chronic exposure to OP pesticides.

A cholinergic crisis (CC) may occur in acute organophosphate intoxication because of AChE inhibition. Symptoms include, but are not limited to, miosis, sweating, lacrimation, gastrointestinal symptoms, respiratory difficulties, dyspnea, bradycardia, cyanosis, vomiting, diarrhea, as well as other symptoms. Along with these central cholinergic effects, seizures, convulsions, coma, and/or respiratory failure are occasionally observed.

An intermediate syndrome (IMS) appears in the interval between the end of a cholinergic crisis and the onset of OPIDP. Symptoms associated with IMS generally manifest within 24-96 hours after exposure. The exact etiology, incidence, and risk factors associated with IMS are not clearly understood, but IMS is recognized as a disorder of neuromuscular junctions. IMS occurs when a person has a prolonged and severe inhibition of AChE. Symptoms generally include, but are not limited to, increasing weakness of facial, neck flexor and respiratory muscles.

Organophosphate-induced delayed polyneuropathy (OPIDP) occurs in a small percentage of cases, roughly two weeks after an untreated exposure, where temporary paralysis develops. Symptomatically, this condition represents a loss of function and ataxia of peripheral nerves and spinal cord. Symptoms generally begin with shooting pains in both legs and become progressively worse over 3-6 months. Treatment at this stage of organophosphate intoxication only affects sensory nerves, whereas motor neuron function is not improved such that a permanent loss of function may result. It should be noted that conventional organophosphate treatments are ineffective for OPIDP. OPIDP induces aging and phosphorylation of more than 70% of functional NTE in peripheral nerves. Jokanovic et al., "Neurotoxic effects in patients poisoned with organophosphate pesticides" *Environmental Toxicology and Pharmacology* 29:195-201 (2010).

Chronic organophosphate-induced neuropsychiatry disorder (COPIND) occurs without persistent cholinergic symptoms and is therefore not dependent on AChE inhibition. COPIND appears with a delay after initial organophosphate intoxication and is long lasting. Symptoms include, but are not limited to, cognitive deficit, mood change, autonomic dysfunction, peripheral neuropathy, and extrapyramidal symptoms. The underlying mechanisms of COPIND have not been determined, but it is hypothesized that the condition may be a withdrawal syndrome subsequent to chronic or acute exposure to an organophosphate compound. Jokanovic et al., "Neurotoxic effects in patients poisoned with organophosphate pesticides" *Environmental Toxicology and Pharmacology* 29:195-201 (2010).

The chronic behavioral dysfunction or deficits that follow nerve agent exposure include persistent elevation in anxiety, irritability, behavioral avoidance, memory deficits, insomnia and other psychiatric manifestations. Five years after the attacks with the nerve agent sarin in Matsumoto and Tokyo, individuals exposed to sarin reported persistent increases in symptoms that characterize anxiety disorders, including irritability and restlessness, avoidance of places that triggered recollection of the trauma, tension, and insomnia. EEG abnormalities indicative of epileptic activity were also present in exposed individuals. In animal models, exposure to nerve agents also results in long-term increases in anxiety and fear-like behavioral patterns. The amygdala plays a central role in the control of emotional behavior and disruptions in neuronal network and excitability have been observed in the basolateral nucleus of the amygdala after 1 to 3 months following the nerve agent exposure. Murata et al. "Asymptomatic sequelae to acute sarin poisoning in the central and autonomic nervous system 6 months after the Tokyo subway attack. *Journal of Neurology* 244: 601-606 (1997); Nishiwaki et al. "Sarin Health Effects Study 2001. Effects of sarin on the nervous system in rescue team staff members and police officers 3 years after the Tokyo subway sarin attack" *Environ Health Perspect* 109: 1169-1173 (2001); Ohtani et al. "Post-traumatic stress disorder symptoms in victims of Tokyo subway attack: a 5-year follow-up study. *Psychiatry Clin Neurosci* 58: 624-629 (2004); Yanagisawa et al. "Sarin experiences in Japan: acute toxicity and long-term effects" *J Neurol Sci* 249: 76-85 (2006); Coubard et al, "Long-term consequences of soman poisoning in mice: part 2. Emotional Behavior" *Behav Brain Research* 191:95-103 (2008); Prager et al "The recovery of acetylcholinesterase activity and the progression of neuropathological and pathophysiological alterations in the rat basolateral amygdala after soman-induced status epilepticus: Relation to anxiety-like behavior" *Neuropharmacology* 81:64-74 (2014).

Exposure to organophosphorus (OF) nerve agents can cause long-term plasticity and secondary damage to the neuronal network and synchronization. As a result of brain damage caused by OP intoxication and acute seizures, the affected areas in the brain undergo neuroplastic processes changing the neuronal circuitry. For example, the axonal sprouting in the inner molecular layer of the hippocampus can occurs after weeks months following OP exposures. Okazaki et al. "Hippocampal mossy fiber sprouting and synapse formation after status epilepticus in rats: visualization after retrograde transport of biocytin" *J Comp Neurol* 352:515-534 (1995).

A major long-term consequence of soman-induced seizures is induction of epileptogenesis and development of acquired epilepsy, characterized by spontaneous recurrent seizures within months or years after OP exposure. There are strong indications on the occurrence of spontaneous seizures, hyperreactivity, and aggressive behavior in rats, and possibly the presence of spontaneous seizures in nonhuman primates. Romano et al. "Health Effects of Low-Level Exposure to Nerve Agents. In Somani S M, Romano J A Jr (Eds) *Chemical Warfare Agents: toxicity at Low Levels*, CRC Press, Boca Raton, Fla., ISBN 0-8493-0872-0, CRC Press, Boca Raton, Fla. (2001); McDonough et al "The intramuscular toxicity of soman in the African Green Monkey. *US Army Medical Research Inst of Chemical Defense Aberdeen Proving Ground Md. Technical Report* A131344 (2004); de Araujo Furtado et al. "Spontaneous recurrent seizures after status epilepticus induced by soman in Sprague-Dawley rats" *Epilepsia* 51:1503-1510 (2010).

Metabolic breakdown of organophosphates is believed to be mediated by the enzyme paraoxonase (PON1) through a hydrolylic mechanism. For example, PON1 may hydrolyze active organophosphate metabolites. Costa, et al., "Measurement of paraoxonase (PON1) status as a potential biomarker of susceptibility to organophosphate toxicity" *Clinica Chimica Acta* 352: 37-47 (2005). PON1 polymorphisms result in different enzyme levels and catalytic efficiency of this esterase, which in turn suggests that different individuals may be more (or less) susceptible to organophosphate intoxication. For example, an increased level of PON1 plasma hydrolytic activity confers resistance to organophosphate intoxication. The catalytic efficiency with which PON1 can degrade toxic Ops also determines the degree of protection that PON1 can provide for organism. The higher the concentration of PON1 the better the protection provided. A 13-fold variation was seen in PON1 levels in adults, as well as, specifically regarding sensitivity to diazoxon, a variation up to 26 and 14-fold was reported in a group of newborns and Latino mothers, Therefore, it is apparent that there is a wide range in variability of enzyme levels that determine human sensitivity to organosphosphate intoxication. US EPA Office of Pesticide Programs, "Organophosphorous Cumulative Risk Assessment 2006 Update" (December 2011).

A number of measurements exist to assess exposure and early biological effects for organophosphate poisoning. Measurements of OP metabolites in both the blood and urine can be used to determine if a person has been exposed to organophosphates. Specifically in the blood, metabolites of cholinesterases, such as butyrylcholinesterase (BuChE) activity in plasma, neuropathy target esterase (NTE) in lymphocytes, and of acetylcholinesterase (AChE) activity in red blood cells. Due to both AChE and BuChE being the main targets of organophosphates, their measurement is widely used as an indication of an exposure to an OP. The main restriction on this type of diagnosis is that depending on the OP the degree to which either AChE or BuChE are inhibited differs; therefore, measure of metabolites in the blood and urine do not specify for a certain OP. However, for fast initial screening, determining AChE and BuChE activity in the blood are the most widely used procedures for confirming a diagnosis of OP poisoning. Worek et al., "Diagnostic aspects of organophosphate poisoning" *J Toxicology* 214: 182-189 (2005).

III. Neurosteroids

Neuroactive steroids, herein referred to as neurosteroids, are endogenous steroids that rapidly alter neuronal excitability through interaction with ligand-gated ion channels and other cell surface receptors, Paul et al., "Neuroactive steroids" *FASEB J.* 6 (6): 2311-2322 (1992); and Lan et al., "Neuroactive steroid actions at the GABA-A-receptor" *Horm Behav* 28 (4):537-544 (1994). Neuroactive steroid refers to steroids that are synthesized by an endocrine gland that then reach the brain through the bloodstream and have effects on brain function. Srivastava et al., "Rapid estrogen signaling in the brain: implications for the fine-tuning of neuronal circuitry". *J. Neurosci.* 31 (45):16056-16063 (2011). In addition to their actions on neuronal membrane receptors, some of these neurosteroids may also exert effects on gene expression via nuclear steroid hormone receptors. Neurosteroids have a wide range of potential clinical applications from sedation to treatment of epilepsy and traumatic brain injury. Reddy et al., "Neurosteroid replacement therapy for catamenial epilepsy" *Neurotherapeutics* 6 (2): 392-401 (2009); Morrow A., "Recent Developments in the Significance and Therapeutic Relevance of Neuroactive Steroids—Introduction to the Special Issue" *Pharmacol. Ther.* 116 (1):1-6 (2007); and Dubrovsky B., "Steroids, neuroactive steroids and neurosteroids in psychopathology" *Prog. Neuropsychopharmacol. Biol. Psychiatry* 29 (2):169-192 (2005). Ganaxolone, a synthetic analog of the endogenous neurosteroid allopregnanolone, may also be useful to treat epilepsy. Bialer M., ""Ganaxolone", In: Progress report on new antiepileptic drugs: a summary of the Eleventh Eilat Conference (EILAT XI)" *Epilepsy Res.* 103 (1): 2-30 (2013).

Some known biological functions of neurosteroids include, but are not limited to, modulation of neural plasticity, learning and memory processes, behavior, seizure susceptibility, stress, anxiety, and depression. Neurosteroids also appear to play an important role in various sexually-dimorphic behaviors and emotional responses. Benarroch E., "Neurosteroids: endogenous modulators of neuronal excitability and plasticity" *Neurology* 68 (12):945-947 (2007). Vallée et al., "Neurosteroids in learning and memory processes" *Int. Rev. Neurobiol.* 46:273-320 (2001); Engel et al., "Neurosteroids and behavior" *Int. Rev. Neurobiol.* 46:321-348 (2001); King S., "Emerging roles for neurosteroids in sexual behavior and function" *J. Androl.* 29 (5):524-533 (2008); Joshi et al., "GABAergic transmission in temporal lobe epilepsy: the role of neurosteroids" *Exp. Neurol.* 244:36-42 (2013); and Girdler et al., "Neurosteroids in the context of stress: implications for depressive disorders" *Pharmacol. Ther.* 116 (1):125-139 (2007).

Acute stress elevates the levels of inhibitory neurosteroids like allopregnanolone, and neurosteroids are known to counteract many of the effects of stress. Chronic stress has been associated with diminished levels of allopregnanolone and altered allopregnanolone stress responsivity, psychiatric disorders, and hypothalamic-pituitary-adrenal axis dysregulation. Bali et al., "Multifunctional aspects of allopregnanolone in stress and related disorders" *Prog. Neuropsychopharmacol. Biol. Psychiatry* 48:64-78 (2014). This is similar to endorphin activity, which are released in response to stress and physical pain and counteract the negative subjective effects of such states. As such, it has been suggested that one of the biological functions of these neuromodulators may be to help maintain emotional homeostasis. Gunn et al., "$GABA_A$ receptor-acting neurosteroids: A role in the development and regulation of the stress response" *Front Neuroendocrinal.* 36:28-48 (2015).

Several synthetic neurosteroids have been used as sedatives for the purpose of general anaesthesia for carrying out surgical procedures. The best known of these are alphaxolone, alphadolone, hydroxydione and minaxolone.

The first of these to be introduced was hydroxydione, which is the esterified 21-hydroxy derivative of 5↑-pregnanedione. Hydroxydione proved to be a useful anaesthetic drug with a good safety profile, but was painful and irritating when injected probably due to poor water solubility. This led to the development of newer neuroactive steroids.

The next drug from this family to be marketed was a mixture of alphaxolone and alphadolone, known as Althesin. This was withdrawn from human use due to rare but serious toxic reactions, but is still used in veterinary medicine.

The next neurosteroid anesthetic introduced into human medicine was the newer drug minaxolone, which is around three times more potent than althesin and retains the favorable safety profile, without the toxicity problems seen with althesin. However this drug was also ultimately withdrawn, not because of problems in clinical use, but because animal studies suggested potential carcinogenicity and since alternative agents were available it was felt that the possible risk outweighed the benefit of keeping the drug on the market.

The neurosteroid ganaxolone, an analog of the progesterone metabolite allopregnanolone, has been extensively investigated in animal models and is currently in clinical trials for the treatment of epilepsy. Neurosteroids, including ganaxolone, have a broad spectrum of activity in animal models. Neurosteroids, such as ganaxolone, may have advantages over other $GABA_A$ receptor modulators, and most notably benzodiazepines, in that tolerance does not appear to occur with extended use. Rogawski et al., "Neurosteroids: endogenous modulators of seizure susceptibility" In: Rho, J. M., Sankar, R., Cavazos, J. (Eds.), Epilepsy: Scientific Foundations of Clinical Practice. Marcel Dekker, New York, 2004; 319-355 (2004); Kokate et al., "Lack of anticonvulsant tolerance to the neuroactive steroid pregnenolone in mice". *J. Pharmacol. Exp. Ther.* 287 (2):553-

558 (1998); Reddy et al., "Chronic treatment with the neuroactive steroid ganaxolone in the rat induces anticonvulsant tolerance to diazepam but not to itself". *J. Pharmacol. Exp. Ther.* 295 (3):1241-1248 (2000).

Benzodiazepines may influence neurosteroid metabolism by virtue of their actions on translocator protein (TSPO; "peripheral benzodiazepine receptor"). The pharmacological actions of benzodiazepines at the $GABA_A$ receptor are similar to these of neurosteroids. Factors which affect the ability of individual benzodiazepines to alter neurosteroid levels may depend upon whether the individual benzodiazepine drug interacts with TSPO. Some benzodiazepines may also affect neurosteroidogenic pathways involved in neurosteroid synthesis. Dhir et al., "Role of neurosteroids in the anticonvulsant activity of midazolam" *Br J Pharmacol* 165 (8):2684-2691 (2011); and Usami et al., "Substrate specificity of human 3(20)alpha-hydroxysteroid dehydrogenase for neurosteroids and its inhibition by benzodiazepines" *Biol Pharm Bull* 25 (4):441-445 (2002). However, the extent of such interactions and its physiological or pharmacological impact on neuronal function remains unclear. Although it is not necessary to understand the mechanism of an invention, it is believed that benzodiazepines act primarily at synaptic GABA-A receptors, which undergo internalization in response to nerve agent-induced seizures; however, extrasynaptic receptors may remain unchanged. Unlike neurosteroids, benzodiazepines may not act at extrasynaptic GABA-A receptors. Reddy et al. "Antiseizure Activity of Midazolam in Mice Lacking δ-Subunit Extrasynaptic GABA-A Receptors" *J Pharmacol Exp Ther.* 353 (3):517-528 (2015).

Neurosteroids are rational and innovative countermeasures for OP intoxication. They are present in the brain as endogenous modulators of seizure susceptibility. Although a variety of neurosteroids are present in the brain, the most widely studied are allopregnanolone (5α-pregnane-3α-ol-20-one), THDOC (5α-pregnane-3α,21-diol-20-one), and androstanediol (5α-androstan-3α-ol-20-diol). They lack conventional hormonal activity and instead rapidly alter excitability through direct interaction with GABA-A receptors. This occurs by binding to "neurosteroid binding sites" on the receptor channel. They can directly activate the receptor and promote maximal inhibition. Neurosteroids act on all GABA-A receptor isoforms in the brain. They potentiate synaptic receptors and also activate δ-subunit-containing extrasynaptic GABA-A receptors that mediate inhibitory tonic currents. The extrasynaptic GABA-A receptors are highly sensitive to neurosteroids and they play a critical role in neuronal network excitability and seizure susceptibility. Reddy "Pharmacology of endogenous neuroactive steroids" *Critical Reviews in Neurobiology* 15: 197-234 (2003); Reddy "Neurosteroids: Endogenous role in the human brain and therapeutic potentials" *Progr Brain Res* 186: 113-137 (201); Carver and Reddy. "Neurosteroid interactions with synaptic and extrasynaptic GABA-A receptors: Regulation of subunit plasticity, phasic and tonic inhibition, and neuronal network excitability" *Psychopharmacology* 230 (2): 151-188 (2013).

Neurosteroids are broad-spectrum anticonvulsants and confer seizure protection in various models. They protect against seizures induced by GABA-A receptor antagonists, 6-Hz model, pilocarpine-induced limbic seizures and seizures in kindled animals. Unlike benzodiazepines, anticonvulsant tolerance is not observed with neurosteroids and they can inhibit epileptogenesis, supporting their superior clinical potential in epilepsy. Although, neurosteroids show promise in the treatment of diverse forms of seizures, no neusosteroid is currently approved by the FDA for clinical use. Ganaxolone, the 3β-methyl analog of allopregnanolone, is a synthetic analog that has additional advantages over the endogenous neurosteroids. Like allopregnanolone, ganaxolone is a potent GABA-A receptor modulator and a broad-spectrum anticonvulsant. Ganaxolone is orally-active, relatively long-acting, and lacks hormonal side effects. In clinical trials, ganaxolone appears to be safe and well-tolerated by oral route in adults, infants, and children. Reddy "Role of anticonvulsant and antiepileptogenic neurosteroids in the pathophysiology and treatment of epilepsy" *Frontiers Endocrinol* 2 (38): 1-11 (2011).

Neurosteroids are novel treatments for nerve agent intoxication and such therapy offers several unique advantages including, but limited to: (i) Neurosteroids can be effective even in diazepam-refractory SE because they can activate most GABA-A receptor isoforms; (ii) Unlike benzodiazepines, neurosteroids lack tolerance upon repeated use; (iii) Neurosteroids show a rapid onset of action & intermediate duration; (iv) Maximal efficacy is expected even in resistant seizures, due to their direct (non-allosteric) actions; (v) They promote tonic inhibition that does not rely on interneurons that are damaged in SE; (vi) They are readily available for practical use in OP threats (ganaxolone is FDA-approved for clinical trials); (vii) They can be effective against a broad spectrum of nerve agents and pesticides, making them broad countermeasures; and (viii) A suitable pharmaceutical formulation would allow preparation of an autoinjector system for rapid use by first responders, and hence they are much more attractive for inclusion in the emergency antidote kit. Kokate et al. "Anticonvulsant activity of neurosteroids: Correlation with γ-aminobutyric acid-evoked chloride current potentiation" *J Pharmacol Exp Ther* 270:1223-1229 (1994); Reddy et al. "Chronic treatment with the neuroactive steroid ganaxolone in the rat induces anticonvulsant tolerance to diazepam but not to itself" *J Pharmacol Exp Therap* 295: 1241-1248 (2000); Reddy et al. "Antiseizure activity of progesterone and neurosteroids in progesterone receptor knockout mice" *J Pharmacol Exp Therap* 310: 230-239 (2004); Reddy "Role of anticonvulsant and antiepileptogenic neurosteroids in the pathophysiology and treatment of epilepsy" *Frontiers Endocrinol* 2 (38): 1-11 (2011); Wohlfarth et al. "Enhanced neurosteroid potentiation of ternary GABA-A receptors containing the delta subunit" *J Neurosci* 22:1541-1549 (2002). Mihalek et al. "Attenuated sensitivity to neuroactive steroids in GABA-A receptor delta subunit, knockout mice" *Proc Natl Acad Sci USA* 96:12905-12910 (1999). Zhan et al. "Enhanced tonic GABA current in normotopic and hilar ectopic dentate granule cells after pilocarpine-reduced status epilepticus" *J Neurophysiol* 102: 670-681 (2009). Carver et al. Perimenstrual-like hormonal regulation of extrasynaptic δ-containing GABA-A receptors mediating tonic inhibition and neurosteroid sensitivity. *J Neurosci* 34 (43):14181-14197 (2014).

Presently, there are few anticonvulsants with delayed or late-stage efficacy against OP intoxication. The clinical use of benzodiazepines such as diazepam or midazolam for nerve gas exposures is limited because they must be given within minutes of an attack to be effective. Neurosteroids can surpass these limitations. Unlike diazepam, they are robust anticonvulsants when administered hours after chemical exposure. Developing a neurosteroid therapy will represent a huge leap forward in our abilities to counteract the benzodiazepine-resistant seizures due to OP intoxication. The therapy is highly innovative and viable because neurosteroid therapy is rational strategy for OP intoxication and neurosteroids are safe in human trials.

Neurosteroids exhibit significant efficacy in OP-like cholinergic refractory SE, which is a hallmark of nerve agent intoxication. There are few anticonvulsants for controlling OP-induced refractory SE, which is characterized by persistent seizures, progressive internalization of synaptic GABA-A receptors, and benzodiazepine resistance. Naylor et al. "Trafficking of GABA-A receptors, loss of inhibition, and a mechanism for pharmacoresistance in status epilepticus" *Journal of Neuroscience* 25:7724-7733 (2005). Neurosteroids are viable and novel anticonvulsants against chemically-induced refractory SE. It is thought that extrasynaptic δ-containing GABA-A receptors that generate tonic inhibition do not internalize during SE, so that neurosteroids, which activate both extrasynaptic and synaptic receptors, could be more effective treatments for SE. In a rodent model of SE, induced by the cholinergic agonist pilocarpine, neurosteroids are highly effective in protecting against SE when given prior to the chemical exposure. There is evidence from studies is a pilcoarpine model of refractory SE in rats. Reddy et al. "Experimental models of status epilepticus and neuronal injury for evaluation of therapeutic interventions" *International Journal of Molecular Sciences* 14:18284-18318 (2013). The neurosteroid THDOC produced rapid and complete termination of SE when given 60-min after SE. THDOC aborted seizures with very little seizure recurrences, a profile that was superior to diazepam. Structure-activity relationship studies showed that analogs with 3-hydroxyl group and 5-H in the α-configuration were more efficacious than their β-epimers. Analogs with 17β-methyl-carbonyl group were more potent than analogs with 17β-hydroxyl group. Ganaxolone was highly effective when given early or late after seizure onset in pilocarpine model of SE; it produced rapid and effective termination of SE with sustained protection. In summary, the robust anticonvulsant and neuroprotective profile of neurosteroids is far superior to benzodiazepines.

IV. Pharmaceutical Compositions

The present invention further provides pharmaceutical compositions (e.g., comprising the compounds described above). The pharmaceutical compositions of the present invention may be administered in a number of ways depending upon whether local or systemic treatment is desired and upon the area to be treated. Administration may be topical (including ophthalmic and to mucous membranes including vaginal and racial delivery), pulmonary (e.g., by inhalation or insufflation of powders or aerosols, including by nebulizer; intratracheal, intranasal, epidermal and transdermal), oral or parenteral. Parenteral administration includes intravenous, intraarterial subcutaneous, intraperitoneal or intramuscular injection, or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and, the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxyomethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of neurosteroids at the cellular level may also be added to the pharmaceutical and other compositions of the present invention. For example, cationic lipids, such as lipofectin (U.S. Pat. No. 5,705,188), cationic glycerol, derivatives, and polycationic molecules, such as polylysine (WO 97/30731), also enhance the cellular uptake of neurosteroids.

The compositions of the present invention may additionally contain other adjunct components conventionally found in pharmaceutical compositions Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual neurosteroids, and can generally be estimated based on $EC_{50}$s or $ED_{50}$s found to be effective in in vitro and in vivo animal models or based on the examples described herein. In general, dosage is from 0.01 µg to 1 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the compound is administered in maintenance doses, ranging from 0.01 µg to 1 g per kg of body weight, once or more daily, to once every 20 years.

V. Kits

In another embodiment, the present invention contemplates kits for the practice of the methods of this invention. The kits preferably include one or more containers containing a composition and/or an administration device for the performance of a method of this invention. The kit can include a container comprising a neurosteroid. The kit can optionally include a container comprising a neurosteroid and an organophosphate antidote. In one embodiment, the organophosphate antidote includes, but is not limited to, atropine and/or pralidoxime. The kit can optionally include at least one administration device. In one embodiment, the administration device includes, but is not limited to, an intravenous injection syringe, a cardiac needle, an inhalation device, an intramuscular injection syringe and/or a subcutaneous injection syringe. The kit can optionally include a pharmaceutically acceptable excipient and/or a delivery vehicle (e.g., a liposome). The reagents may be provided suspended in the excipient and/or delivery vehicle or may be provided as a separate component which can be later combined with the excipient and/or delivery vehicle. The kit may optionally contain additional therapeutics to be co-administered with the neurosteroid.

The kits may also optionally include appropriate systems (e.g. opaque containers) or stabilizers (e.g. antioxidants) to present degradation of the reagents by light or other adverse conditions.

The kits may optionally include instructional materials containing directions (i.e., protocols) providing for the use of the neurosteroids in the treatment of organophosphate intoxication. Instructions optionally comprise specific treatment protocols for cholinergic crisis in contrast to non-cholinergic crisis. While the instructional materials typically comprise written or printed materials they are not limited to such. Any medium capable of storing such instructions and communicating them to an end user Is contemplated by tins invention. Such media include, but are not limited to electronic storage media (e.g., magnetic discs, tapes, cartridges, chips), optical media (e.g., CD ROM), and the like. Such media may include addresses to internet sites that provide such instructional materials.

EXPERIMENTAL

Example 1

Neurosteroid Inhibition of Organophosphate Nerve Agent Intoxication

This example demonstrates that ganaxolone treatment terminates the nerve agent soman (GD)-induced organophosphate intoxication manifestations when given at 40-min, 60-min or 120-min after exposure in rats.

Methods: The nerve agent studies were conducted as per the established MRICD protocol in rat models. Apland et al. "Higher susceptibility of the ventral versus the dorsal hippocampus and the posteroventral versus anterodorsal amygdala to soman-induced neuropathology" *Neurotoxicology* 31 (5):485-492 (2010). Rats implanted with EEG recording electrodes were exposed to soman (154 µk/kg, $1.4 \times LD_{50}$) by a single subcutaneous injection, as per the USMRICD protocol. The peripheral cholinesterase reactivator HI-6 (125 mg/kg, i.p.) was given 30-min prior to soman to increase the survival rate. Within 1 min of soman exposure, all rats received atropine methylnitrate (2 mg/kg, i.m.) to minimize peripheral toxic effects. HI-6 and atropine do not directly affect seizures since they do not cross the BBB. This regimen is consistent with the U.S. Army antidote for nerve agents. The protective efficacy of test drugs in terminating DFP or soman-induced SE and seizure activity was assessed using four key parameters: (a) severity of behavioral seizures; (b) frequency of electrographic spikes; (c) cumulative duration of seizure activity; and (d) latency to termination of seizure activity.

Figure 3:
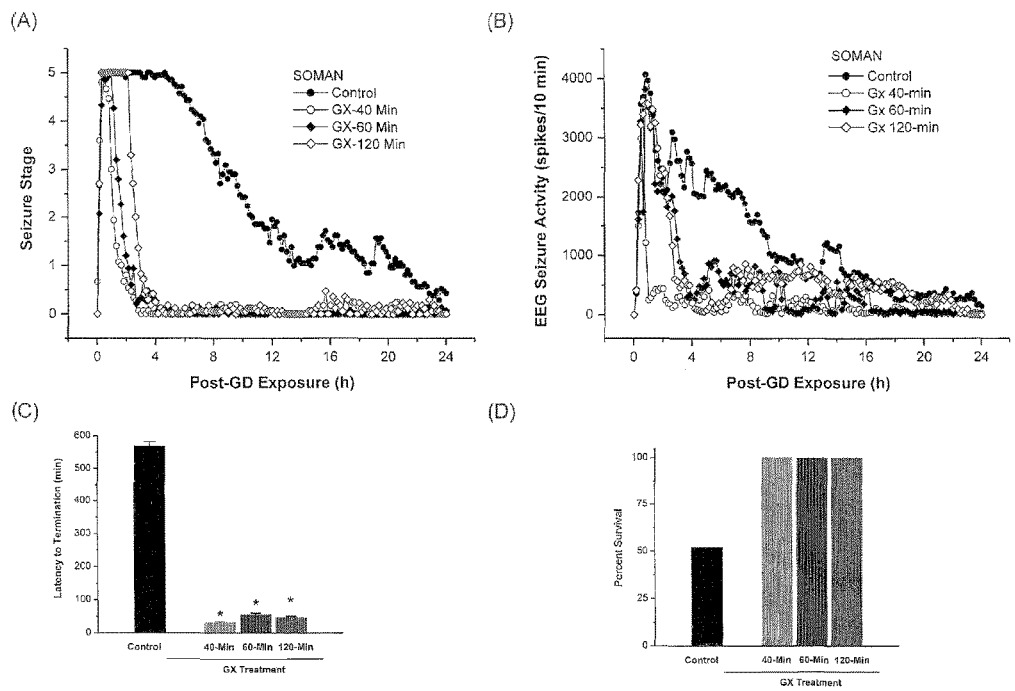
FIG. 3A-D presents efficacy of delayed treatment with ganaxolone (10 mg/kg, IM) against the nerve agent soman-induced OP intoxication, seizures and status epilepticus. (A) Time-course behavioral profile of protective activity of ganaxolone against OP intoxication caused by soman exposure in rats. (B) Time-course EEG profile of protective activity of ganaxolone against OP intoxication caused by soman exposure in rats. (C) Latency for termination of somam-induced seizures or status epilepticus by ganaxolone treatment in rats. (D) Mortality rate in control (untreated) and ganaxolone treatment groups in the soman model. Ganaxolone was given at 40, 60 or 120 min after soman exposure and behavioral stages and EEG seizure activity were monitored continuously for 24 h. Data presented as mean or mean±SEM (n=7 to 12 rats in each group). *P<0.01 as compared to control group as determined by one-way ANOVA with post hoc student's t-test.

Results: Ganaxolone was given to rats intramuscularly (im) at 40 min, 60 min or 120 min after soman administration. The data showed that ganaxolone (10 mg/kg, im) effectively controlled electrographic and behavioral activity within 40 to 60 min after treatment with very little seizure recurrences. Ganaxolone-treated rats (40 minute post-exposure) had a 100% survival rate, unlike the untreated control rats that exhibited a 50% mortality rate. Thus, ganaxolone has a powerful protective activity against the nerve agent soman-induced neurotoxic manifestations even after delayed treatment regimen. See, FIG. 3.

Example 2

Neurosteroid Inhibition of Organophosphate Nerve Agent-Induced Neuronal Injury Neurodegeneration, and Neuroinflammation The example demonstrates that ganaxolone treatment protects against the nerve agent soman (GD)-induced organophosphate intoxication brain injury and neurodegeneration when given at 40-min, 60-min or 120-min after exposure in rats.

Methods: The neuroprotectant efficacy of ganaxolone treatment was assessed by an immunohistochemical staining and quantitative analysis of brain sections using four specific markers; (a) neuronal injury (FJB); (b) principal neuronal loss (NeuN); (c) interneuron loss (PV); and (d) neuroinflammation (astrocytic response by GFAP) in key brain regions including the hippocampus, amygdala, cortex, and other areas. Quantitative histology studies were utilized for characterization of the time-dependent protective ability of ganaxolone (10 mg/kg, im) against GD-induced neuronal injury, neuronal cell death, and neurodegeneration. (i) Neuronal injury: To assess neuroprotective effect of ganaxolone against GD-induced cellular and neuronal death, acute histological outcome was assessed at 24 hours after GD. Animals were euthanized for histological analysis of neuronal death by Fluoro-Jade-B (FJB) and Nissl staining. Brains were fixed by paraformaldehyde perfusion and cut 30-µm thick sections using cryostat. They were then processed in serial sections for FJB staining and quantified the absolute numbers of FJB(+) neurons in hippocampal subfields, and other regions. (ii) Neurodegeneration: The extent of neuronal damage was quantified by staining serial sections with the mature neuronal marker NeuN, and the interneuron markers parvalbumin (PV). The absolute numbers of principal neurons and interneurons and the relative neuroprotection were calculated using the neurostereology technique. (iii) Neuroinflammation: The extent of inflammation response was quantified by immunostaining for GFAP, a standard astrocytic activation marker in the brain. The area fractionation approach was utilized to determine the extent of GFAP expression and the relative neuroprotection was calculated using the normalization with non-GD controls.

Figure 4:
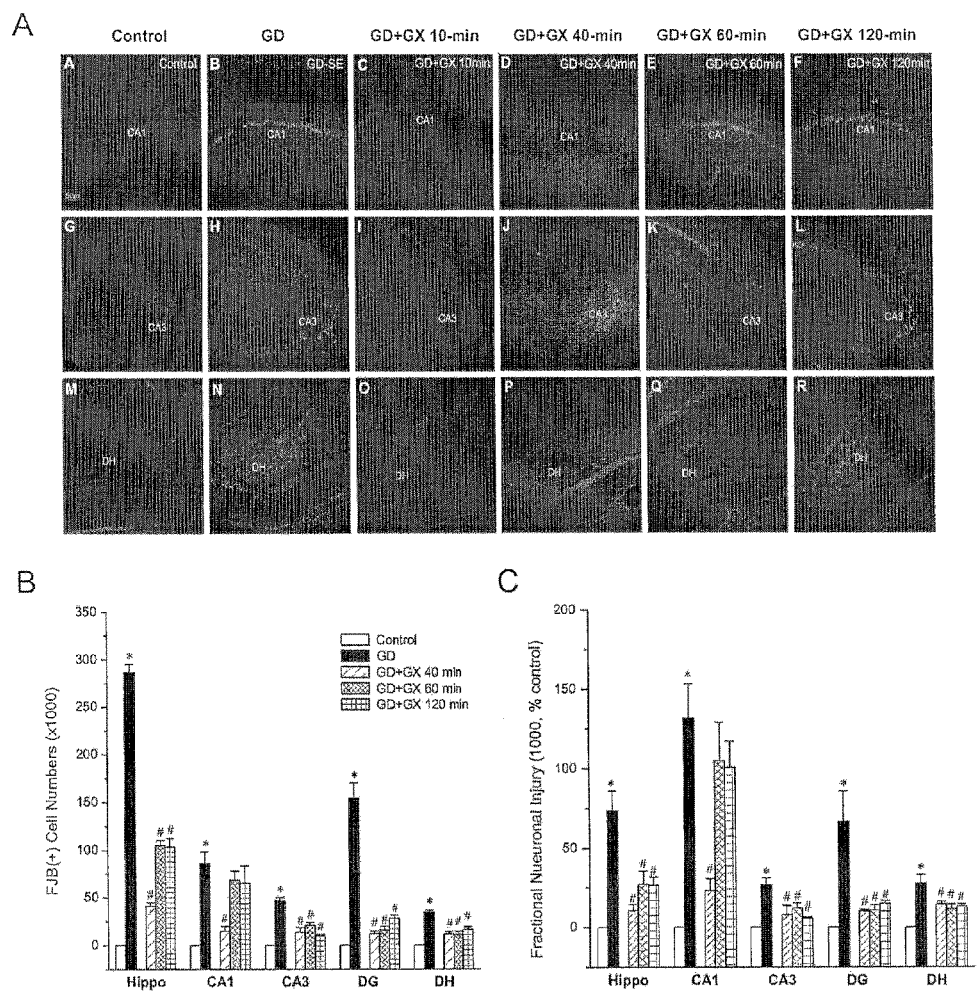
FIG. 4A-C presents efficacy of delayed treatment with ganaxolone (10 mg/kg, IM) against the nerve agent soman-induced OP intoxication related acute neuronal damage within the brain hippocampus subfields CA1, CA3 and dentate hilus. (A) Time-course profile of neuroprotectant activity ganaxolone treatment in the soman model to rats. Representative confocal images show FJB-positive neurons within the hippocampus subfields. (B) Absolute quantification of FJB-positive cell counts in the hippocampus subfields as determined unbiased neurostereology technique. Data represent mean±SEM (N=4-6 rats per group). (C) Protective effect of ganaxolone on acute neuronal injury as determined by percent of FJB-positive cell counts in the hippocampus subfields as compared to control group. Data represent mean±SEM (N=4-6 rats per group). *P<0.01 as compared to control group as determined by one-way ANOVA with post hoc student's t-test.
Figure 5:
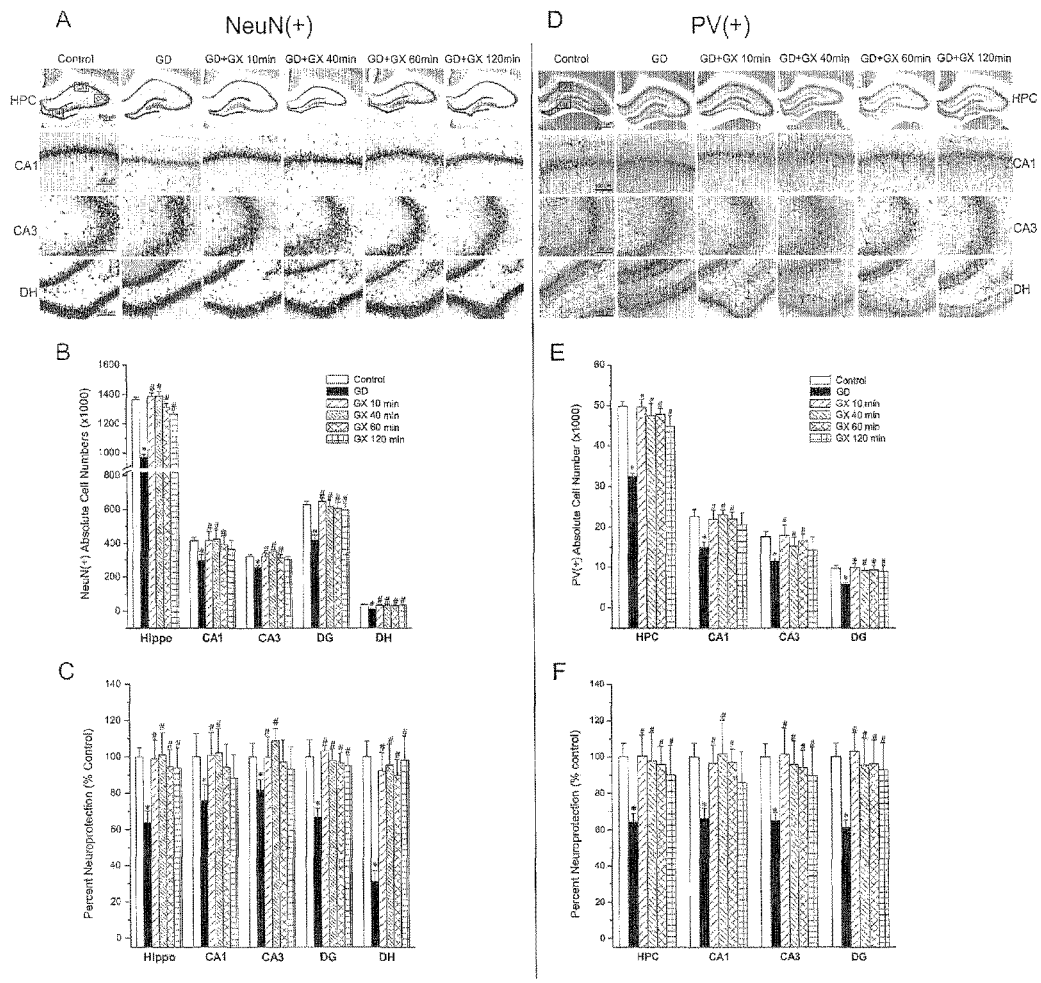
FIG. 5A-F presents the neuroprotectant activity of delayed ganaxolone treatment (10 mg/kg, IM) in soman-induced neuronal cell death and neurodegeneration in rats.

Results: Rats were treated in accordance with Example 1, where the data demonstrated that ganaxolone had neuroprotectant efficacy by reducing acute neuronal injury, neuronal cell death, and neurodegeneration when administered 40 minutes or later after soman exposure. In vehicle control or untreated group, soman exposure caused massive or extensive neuronal injury in the hippocampus and other brain regions as revealed by FJB staining. Ganaxolone treatment (40 min or later after soman) significantly (>75%) prevented acute neuronal injury assessed by FJB-positive cell counts. Ganaxolone therapy significantly reduced (>90%) cell death of principal neurons as assessed by NeuN staining, and markedly decreased the cell death of interneurons (>85%) as assessed by parvalbumin (PV) staining and unbiased quantitative stereology. Ganaxolone treatment (40 min post-GD) significantly reduced neuroinflammation as assessed by GFAP-positive staining. Thus, ganaxolone has a strong neuroprotectant activity even after delayed treatment after soman exposure. See, FIG. 4, FIG. 5, and FIG. 6.

Example 3

Inhibition of the Nerve Agent Soman Intoxication by a Variety of Neurosteroids

This example demonstrates that treatment with a variety of neurosteroids (allopregnanolone, THDOC, alfaxolone and androstanediol) terminates the nerve agent soman (GD)-induced organophosphate intoxication manifestations when given at 40-min after exposure in rats.

Methods: The nerve agent studies were conducted as per the Method described in Example 1.

Figure 7:
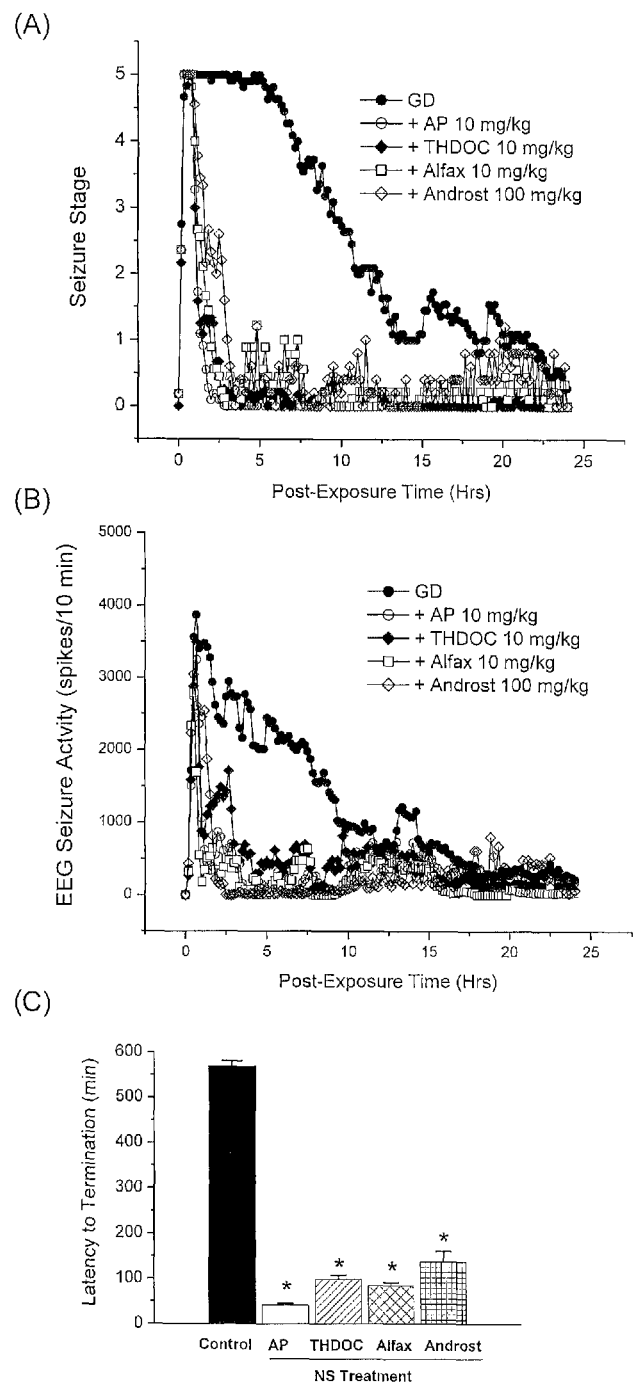

Results: The neurosteroid allopregnanolone (10 mg/kg, im), THDOC (10 mg/kg, im), alfaxolone (10 mg/kg, im) or androstanediol (100 mg/kg, im) was given to rats intramuscularly (im) at 40 min after soman administration. The data showed that test neurosteroids effectively controlled electrographic and behavioral activity within 40 to 60 min after treatment with very little seizure recurrences. The ability of these four test neurosteroids is comparable to that of ganaxolone (Example 1). Thus, neurosteroids that are structural analogs or bear similar features to ganaxolone have a powerful protective activity against the nerve agent soman-induced neurotoxic manifestations even after delayed treatment regimen. See. FIG. 7.

Example 4

Inhibition of the Nerve Agent Soman-Induced Neuronal Injury, Neurodegeneration, and Neuroinflammation by a Variety of Neurosteroids This example demonstrates that treatment with a variety of neurosteroids (allopregnanolone, THDOC, alfaxolone and androstanediol) terminates the nerve agent soman (GD)-induced organophosphate intoxication brain injury and neuronal cell death when given at 40-min after exposure in rats.

Methods: The nerve agent studies were conducted as per the Method described in Example 2.

Results: Rats were treated in accordance with Example 3, where the data demonstrated that all four test neurosteroids had neuroprotectant efficacy by reducing acute neuronal injury and neuronal cell death when administered 40 minutes after soman exposure. In vehicle control or untreated group, soman exposure caused massive or extensive neuronal injury in the hippocampus and other brain regions as revealed by FJB staining. The neurosteroid allopregnanolone, THDOC, alfaxolone and androstanediol treatment significantly prevented acute neuronal injury assessed by FJB-positive cell counts. All four test neurosteroids significantly reduced the fractional cell death as assessed by FJB(+) staining and unbiased quantitative stereology. Thus, neurosteroids that are structural analogs or with similar features of ganaxolone have a strong neuroprotectant activity even after delayed treatment after soman exposure. See, FIG. 8.

Example 5

Neurosteroid Vs. Benzodiazepine Inhibition of Organophosphate Nerve Agent Intoxication This example demonstrates that ganaxolone alone or in combination therapy with midazolam is more effective than midazolam alone when administered 40 minutes after soman exposure in rats.

Methods: The nerve agent studies were conducted as per the Method described in Example 1. Midazolam alone or multiple combination regimens of ganaxolone and midazolam were tested in the soman model.

Results: Midazolam (2 mg/kg, im), ganaxolone (6 & 10 mg/kg, im) or a combination regimen consisting of both drugs was given to rats intramuscularly (im) at 40 min after soman administration. The data showed that midazolam alone (2 mg/kg, im) failed to protect against soman-induced seizures at 40-min post-soman. Ganaxolone (10 mg/kg, im) effectively controlled electrographic and behavioral activity within 40 to 60 min after treatment with very little seizure recurrences (see Example 1), indicating a superior protectant efficacy of ganaxolone than midazolam. As compared to midazolam alone, a combination regimen of low-dose (6 mg/kg, im) and standard-dose (10 mg/kg, im) ganaxolone+midazolam displayed a superior anticonvulsant efficacy with complete seizure termination within 15-25 min. Such combination produced a greater protectant efficacy than midazolam monotherapy.

Example 6

Neurosteroid Inhibition of the Nerve Agent VX Intoxication

This example demonstrates that ganaxolone treatment terminates the V-series nerve agent VX-induced organophosphate intoxication manifestations when given at 40-min after exposure in rats. Unlike GD, the nerve agent VX has a variable and delayed absorption toxicokinetics, which may have implications for treatment regimens. This example, therefore, demonstrates the likely extension of therapeutic scope of ganaxolone for broad-spectrum indications including the low-volatile V-series nerve agents, such as VX.

Methods: The nerve agent VX studies were conducted as per the MRICD models in rats. Male Sprague-Dawley rats implanted with EEG recording electrodes were exposed to VX (26 μg/kg, 1.6×$LD_{50}$) by a single subcutaneous injection. The peripheral cholinesterase reactivator HI-6 (125 mg/kg, i.p.) or 2-PAM (25 mg/kg, i.m.) was given to increase the survival rate. Within 1 min of VX exposure, rats will receive atropine methyl nitrate (2 mg/kg, i.m.) to minimize peripheral toxic effects. Ganaxolone (10 mg/kg, i.m.) was given 40 min after exposure to VX. The protective efficacy of ganaxolone in terminating DFP or soman-induced SE and seizure activity was assessed using four key parameters: (a) severity of behavioral seizures; (b) frequency of electrographic spikes; (c) cumulative duration of seizure activity; and (d) latency to termination of seizure activity.

Results: Ganaxolone was given to rats intramuscularly (im) at 40 min after VX administration. The data showed that ganaxolone (10 mg/kg, im) effectively controlled electrographic and behavioral activity within 40 to 60 min after treatment with very little seizure recurrences. Ganaxolone-treated rats (40 minute post-exposure) had an improved survival rate, similar to the GD model results in Example 1. Thus, ganaxolone has a strong protective activity against the nerve agent VX-induced neurotoxic manifestations even after delayed treatment regimen. See, FIG. 10.

Example 7

Neurosteroid Inhibition of the Nerve Agent VX-Induced Neuronal Injury and Neurodegeneration The example demonstrates that ganaxolone treatment protects against the nerve agent VX-induced organophosphate intoxication brain injury and neurodegeneration when given at 40-min after exposure in rats.

Methods: The nerve agent VX studies were conducted as per the Methods in Example 6 and neuroprotection assessment was made as per the Methods described in Example 2.

Results: Rats were treated in accordance with Example 6, where the data demonstrated that ganaxolone had neuroprotectant efficacy by reducing acute neuronal injury and neuronal cell death when administered 40 minutes after VX exposure. In vehicle control or on treated group, soman exposure caused massive or extensive neuronal injury in the hippocampus CA1 regions as revealed by FJB staining. Ganaxolone treatment significantly prevented acute neuronal injury assessed by FJB-positive cell counts. Ganaxolone significantly reduced the fractional cell death as assessed by FJB(+) staining and unbiased quantitative stereology. Thus, like in the GD model, ganaxolone has a strong neuroprotectant activity even after delayed treatment after VX exposure. See, FIG. 11.

Example 8

Neurosteroid Inhibition of Organophosphate Pesticide Intoxication

This example demonstrates that ganaxolone treatment terminates the pesticide diisopropyl-fluorophosphate (DFP)-induced organophosphate intoxication manifestations when given at 40, 60 or 120-min after exposure in rats.

Methods: We utilized a DFP-induced OP intoxication protocol that is established in our lab as per previously published report. Deshpande et al. "Development of a prolonged calcium plateau in hippocampal neurons in rats surviving status epilepticus induced by the organophosphate DFP" *Toxicol Sci* 116 (2):623-631 (2010). It involves injection of DFP (3.1 mg/kg, sc) to induce persistent seizures and SE in rats. Animals were pretreated with pyridostigmine bromide (0.026 mg/kg, im) 30 min before DFP injection. One minute following DFP injection, animals were given 2-PAM (23 mg/kg, im) and atropine methylnitrate (4 mg/kg, im) to increase the survival rates without affecting severity of seizures since atropine and 2-PAM do not cross the blood-brain barrier. This regimen is consistent with the U.S. Army antidote for OP intoxication. Behavioral and EEG activity was monitored continuously for 24 h to assess the seizure activity. Ganaxolone (1.25-10 mg/kg, im) treatment was initiated at 40 min following DFP. This interval is consistent with antidote objectives for delayed drug therapy after OP exposure.

Results: Ganaxolone was given to rats intramuscularly (im) 40 min, 60 min or 120 min after DFP administration. Ganaxolone (6-10 mg/kg, im) effectively controlled electrographic and behavioral activity within 1 h after treatment with very little seizure recurrences. General neurological assessment for OP intoxication signs and mortality rates were recorded for drug treatment groups at various time intervals. Untreated animals exhibited 50% mortality following DFP and animals that received ganaxolone at 40-min or later all survived, indicating an almost 100% survival rate. Ganaxolone (1.5-10 mg/kg, im) when given 40-min after DFP, produced a dose-dependent protection against DFP-induced OP manifestations with an $ED_{50}$ of 4.8 mg/kg. Thus, ganaxolone has a powerful protectant activity even after delayed treatment after DFP exposure. See, FIG. 12.

Example 9

Neurosteroid Inhibition of Organophosphate Pesticide-Induced Neurodegeneration

This example demonstrates that ganaxolone treatment protects against the pesticide DFP-induced organophosphate intoxication brain injury and neurodegeneration when given at 40, 60or 120-min after exposure in rats.

Methods: The neuroprotectant efficacy of ganaxolone treatment was assessed in accordance with Example 2.

Results: Rats were treated in accordance with Example 8, wherein the data demonstrated neuroprotectant efficacy of ganaxolone in reducing acute neuronal injury, neuronal cell death, and chronic neurodegeneration when administered 40 minutes or later after soman exposure. In vehicle control or untreated group, DFP caused extensive neuronal injury the hippocampus and other brain regions as revealed by FJB staining. Ganaxolone treatment (40 min or later after DFP) almost completely (>90%) prevented neuronal injury assessed by FJB-positive cell counts. Ganaxolone therapy significantly reduced (>75%) cell death of principal neurons as assessed by NeuN staining, and markedly decreased the cell death of interneurons (>70%) as assessed by parvalbumin staining and stereology counting. Using unbiased quantitative stereology, we found >60% reduction in neurodegeneration of principal cells and interneurons at 3 months after DFP challenge. Thus, ganaxolone has a strong neuroprotectant activity in OP pesticide exposure even after delayed treatment at 40 min or later. See, FIG. 13 and FIG. 14.

Example 10

Neurosteroid Inhibition of Organophasphate Pesticide Intoxication is Superior than Midazolam This example demonstrates the superior therapeutic effects of ganaxolone treatment than benzodiazepine midazolam against the pesticide DFP-induced organophosphate intoxication manifestations when given at 40-min or later after exposure in rats.

Methods: The protectant efficacy of ganaxolone treatment against seizures and SE was assessed in accordance with Example 8. To determine whether ganaxolone is superior to diazepam and if a combination of these drugs is superior to monotherapy, we characterized the comparative efficacy of ganaxolone and midazolam in a dose-dependent fashion.

Results: As compared to midazolam (1-5 mg/kg, im) alone, which was only partially effective even at high doses when given at 40 min after DFP, ganaxolone (1.25-10 mg/kg, im) displayed a superior anticonvulsant efficacy due to maximal response in therapeutic protective curve ($ED_{50}$, 4.8 mg/kg). In contrast, midazolam at the highest or toxic dose (5 mg/kg) produced a moderate 45% maximal protection ($ED_{50}$ could not reached), indicating a failure or lack of clinical effectiveness in terminating or controlling OP intoxication seizures in a delayed treatment regimen. Ganaxolone (6 mg/kg, im), when given 40-min after DFP, effectively terminated seizures and SE within 1 h after treatment with very little seizure recurrences. Thus, ganaxolone therapy offers a superior protection than midazolam against OP intoxication in a delayed treatment regimen. See, FIG. 15.

Example 11

Neurosteroid Attenuation of Organophosphate Nerve Agent-Induced Long-Term Neuropsychiatric Dysfunction This example demonstrates that ganaxolone treatment prevents or attenuates against the late-onset or long-term neuropsychiatric deficits caused by the nerve agent Soman-induced organophosphate intoxication when given at 40-min after exposure in rats.

Methods: The neuropsychiatric attenuating efficacy of ganaxolone treatment was assessed using distinct neurological and behavioral assessments. (i) Epileptogenic events. Epileptogenic events were recorded by video-EEG monitoring of rats from 1 to 3 months post-soman exposure. Seizures and epileptiform events and clinical or subclinical events scored for occurrence, frequency and severity. (ii) Memory dysfunction. To test whether cognitive function is impaired in rats exposed to soman, groups of rats were subjected to soman exposure and neurological behavior was assayed at 3 months post-exposure by novel object recognition test (NORT), a standard tool for determination of non-spatial memory function in rats.

Results: Rats were treated in accordance with Example 1, wherein the data demonstrated protectant efficacy of ganaxolone in preventing or attenuating functional memory deficits and epileptogenesis when administered 40 minutes or later after soman exposure. In vehicle control or untreated group, soman caused a long-term epileptogenic response with spontaneous seizures in up to 75% animals at 3-months post-soman exposure. Ganaxolone treatment (6 & 10 mg/kg, im) significantly prevented the occurrence of epilepsy development. Ganaxolone therapy modified the epileptogenesis as evident by reduced EEG seizure intensity compared to soman control. In the NORT, the memory impairment caused by soman exposure at 3 months post-exposure was attenuated in ganaxolone-treated group. Thus, ganaxolone therapy has the potential to attenuate or prevent the long-term neuropsychiatric manifestations of OP nerve agent exposure even after delayed treatment at 40 min or later. See, FIG. 16.

Example 12

Neurosteroid Pharmacokinetics During Organophosphate Compound Intoxication

This example demonstrates the pharmacokinetic (PK) evaluation of intramuscular ganaxolone formulation in naïve rats and in rats following soman or DFP exposure.

Methods. Ganaxolone pharmacokinetic values were determined in rats following a single intravenous (iv) or intramuscular (im) administration under various models of organophosphate compound intoxication. Rats received a single iv or im dose of ganaxolone at 6 mg/kg. Blood and brain samples were collected from rats at 5, 15 and 30 minutes, and 1, 2, 4, 8 and 24 hours post-dose for processing to plasma. Clinical observations were performed immediately post-dose and ~8 hr post-dose.

Results. All animals in the ganaxolone treatment dose group all appeared normal throughout the duration of the study. Plasma samples were analyzed by LC-MS/MS for ganaxolone levels. Pharmacokinetic parameters were calculated using Phoenix WinNonlin (v 6.3). Non-compartmental and compartmental analysis of the plasma drug concentrations was performed. In the iv group, the concentration of ganaxolone at the first time point was 4813 ng/ml and $C_0$ was 7682 ng/ml. The elimination phase $t_{1/2}$ was 4.6 hr and total clearance (Cl) was high, 3883 ml/hr/kg. The $V_d$, 25712 ml/kg, was indicative of extensive tissue distribution. The $AUC_{last}$ was 1324 hr·ng/ml and $AUC_{inf}$ was 1545 hr·ng/ml. After im administration, ganaxolone distribution to plasma was rapid, with a peak plasma concentration ($C_{max}$) of 603 ng/ml, at 0.167 hr ($T_{max}$). The compartmental parameters, $k_a$ and $k_e$, were estimated to be 0.327±0.0280 $hr^{-1}$ and 10.0±3.43 $hr^{-1}$. Group $AUC_{last}$ was 1456 hr·ng/ml and $AUC_{inf}$ was 1614 hr·ng/ml. The $t_{1/2}$ was 2.4 hr. The bioavailability after an im dose of 6 mg/kg was essentially 100%.

Pharmacokinetic parameters of ganaxolone in plasma and brain, of soman, exposed, male Sprague Dawley rats administered a single im dose of 6 mg/kg of ganaxolone are analyzed from plasma- and brain-concentration time curves. After im administration, ganaxolone distribution was rapid, with peak concentrations ($C_{max}$) of 1280±233 ng/ml and 1570±128 ng/g, reached at 0.2-0.3 hr ($T_{max}$) after the 6 mg/kg dose in plasma and brain, respectively. $AUC_{inf}$ in plasma was 1960 hr·ng/ml and notably higher in brain at 4990 hr·ng/g, giving a brain to plasma ratio of 2.6. The elimination half-life values were similar in plasma and brain at 3.3 and 2.6 hr, respectively. Brain concentrations were consistently higher than plasma after 10 min, with a brain to plasma exposure ratio of 2.6. See, FIG. 17

I claim:
1. A method, comprising:
 a) providing;
  i) a subject exhibiting an organophosphate-induced cholinergic crisis, wherein said cholinergic crisis comprises a plurality of symptoms, wherein said plurality of symptoms comprise at least one nicotinic receptor overstimulation symptom; and ii) a composition comprising a neurosteroid and a pharmaceutical carrier; and b) administering an effective amount of said composition to said subject under conditions such that said plurality of symptoms are reduced, wherein said administering is selected from the group consisting of parenteral, intramuscular, subcutaneous, intravenous, inhalation, percutaneous and rectal.

2. The method of claim 1, wherein said composition consists of a neurosteroid and a pharmaceutical carrier.

3. The method of claim 1, wherein said composition is administered less than forty (40) minutes after said organophosphate compound exposure.

4. The method of claim 1, wherein said composition is administered at forty (40) minutes or later after said organophosphate compound exposure.

5. The method of claim 1, wherein said composition is administered between forty (40) minutes and two (2) hours after said organophosphate compound exposure.

6. The method of claim 1, wherein said plurality of symptoms comprise bradycardia, hypotension, bronchorrhoea, salivation, emesis, diarrhea, abdominal pain, urinary frequency, and cardiac rhythm disturbance.

7. The method of claim 1, wherein said plurality of symptoms comprise muscular weakness, muscular paralysis, respiratory insufficiency, and pallor perspiration.

8. The method of claim 1, wherein said plurality of symptoms comprises consciousness alteration, hallucinations, hyperexcitability, synchronous discharges, respiratory centre inhibition and skeletal muscle paralysis.

9. The method of claim 1, wherein said plurality of symptoms further comprises type II paralysis.

10. The method of claim 1, wherein said organophosphate compound is a nerve agent.

11. The method of claim 1, wherein said organophosphate compound is a pesticide.

12. The method of claim 1, wherein said neurosteroid is ganaxolone.

13. The method of claim 1, wherein said neurosteroid is selected from the group consisting of pregnanolone, allopregnanolone, allotetrahydrodeoxycorticosterone, alfaxolone, androstanediol, and related neurosteroidal agents.

14. The method of claim 10, wherein said nerve agent is soman.

15. The method of claim 10, wherein said nerve agent is selected from the group consisting of O-ethyl S-[2-(diisopropylamino)ethyl] methylphosphonothioate (VX) and related chemical agents.

16. The method of claim 11, wherein said pesticide is diisopropyl-fluorophosphate.

17. The method of claim 1, wherein the said pharmaceutical composition has an improved effectiveness to reduce said cholinergic crisis than benzodiazepine agents selected from the group consists of midazolam, diazepam and lorazepam.

18. A method, comprising:
a) providing;
  i) a subject exhibiting at least one symptom of an organophosphate compound-induced non-cholinergic crisis; and
  ii) a composition comprising a neurosteroid and a pharmaceutical carrier; and
b) administering an effective amount of said composition to said subject under conditions such that said at least one symptom of said non-cholinergic crisis is reduced, wherein said administering is selected from the group consisting of parenteral, intramuscular, subcutaneous, intravenous, inhalation, percutaneous and rectal.

19. The method of claim 18, wherein said composition consists of said neurosteroid and said pharmaceutical carrier.

20. The method of claim 18, wherein said composition is administered less than forty (40) minutes after said organophosphate compound exposure.

21. The method of claim 18, wherein said at least one symptom of said non-cholinergic crisis comprises a benzodiazepine-refractory intoxication symptom.

22. The method of claim 18, wherein said at least one symptom of said non-cholinergic crisis is selected from the group consisting of cerebral edema, blood barrier dysfunction, neural inflammation, non-neural inflammation, neuronal cell apoptosis, neuronal cell necrosis, neuronal cell injury, neuronal cell death, neuronal cell loss, axonal degeneration, axonal sprouting and neurodegeneration.

23. The method of claim 18, wherein said at least one symptom of said non-cholinergic crisis is selected from the group consisting of subacute behavioral dysfunction, subacute neurological dysfunction, individual neuropsychiatric disorders and clustered neuropsychiatric disorders.

24. The method of claim 18, wherein said organophosphate compound is a nerve agent.

25. The method of claim 18, wherein said organophosphate compound is a pesticide.

26. The method of claim 18, wherein said neurosteroid is ganaxolone.

27. The method of claim 18, wherein said neurosteroid is selected from the group consisting of pregnanolone, allopregnanolone, allotetrahydrodeoxycorticosterone, alfaxolone, androstanediol, and related neurosteroidal agents.

28. The method of claim 24, wherein said nerve agent is soman.

29. The method of claim 25, wherein said pesticide is diisopropyl-fluorophosphate.

30. The method of claim 18, wherein said pharmaceutical composition has an improved effectiveness to reduce said non-cholinergic crisis than benzodiazepine agents selected from the group consisting of midazolam, diazepam and lorazepam.

31. A method, comprising:
a) providing;
  i) a subject exhibiting at least one late-onset or long-term neuropsychiatric symptom of an organophosphate compound-induced cholinergic crisis or an organophosphate compound-induced non-cholinergic crisis; and
  ii) a composition comprising a neurosteroid and a pharmaceutical carrier; and
b) administering an effective amount of said composition to said subject under conditions such that said at least one late-onset or long-term neuropsychiatric symptom is reduced, wherein said administering is selected from the group consisting of parenteral, intramuscular, subcutaneous, intravenous, inhalation, percutaneous and rectal.

32. The method of claim 31, wherein said composition consists of said neurosteroid and said pharmaceutical carrier.

33. The method of claim 31, wherein said composition is administered less than forty (40) minutes after said organophosphate compound exposure.

34. The method of claim 31, wherein said composition is administered at forty (40) minutes or later after said organophosphate compound exposure.

35. The method of claim 31, wherein said composition is administered between forty (40) minutes and two (2) hours after said organophosphate compound exposure.

36. The method of claim 31, wherein said at least one late-onset symptom is selected from the group consisting of chronic behavioral dysfunction, neurological deficit, cognitive dysfunction, epileptogenic manifestation, and mossy fiber sprouting.

37. The method of claim 31, wherein said at least one late-onset symptom is selected from the group consisting of cerebral edema, blood barrier dysfunction, neural inflammation, non-neural inflammation, neuronal cell apoptosis, neuronal cell death, neuronal cell loss, axonal degeneration, abnormal neurogenesis, axonal sprouting and neurodegeneration.

38. The method of claim 31, wherein said at least one late-onset symptom is selected from the group consisting of behavioral dysfunction, neurological dysfunction, individual neuropsychiatric disorders and clustered neuropsychiatric disorders.

39. The method of claim 31, wherein said organophosphate compound is a nerve agent.

40. The method of claim 31, wherein said organophosphate compound is a pesticide.

41. The method of claim 31, wherein said neurosteroid is ganaxolone.

42. The method of claim 31, wherein said neurosteroid is selected from the group consisting of pregnanolone, allopregnanolone, allotetrahydrodeoxycorticosterone, alfaxolone, androstanediol, and related neurosteroidal agents.

43. The method of claim 39, wherein said nerve agent is soman.

44. The method of claim 39, wherein said nerve agent is selected from the group consisting of O-ethyl S-[2-(diisopropylamino) ethyl] methylphosphonothioate (VX) and related chemical agents.

45. The method of claim 40, wherein said pesticide is diisopropyl-fluorophosphate.

46. The method of claim 31, wherein the said pharmaceutical composition has an improved effectiveness to reduce said late-onset symptoms than a benzodiazepine agent selected from the group consisting of midazolam, diazepam and lorazepam.

* * * * *